US 6,641,592 B1

(12) United States Patent
Sauer et al.

(10) Patent No.: US 6,641,592 B1
(45) Date of Patent: Nov. 4, 2003

(54) SYSTEM FOR WOUND CLOSURE

(75) Inventors: Jude S. Sauer, Pittsford, NY (US);
John F. Hammond, Canandaigua, NY (US)

(73) Assignee: LSI Solutions, Inc., Victor, NY (US)

( * ) Notice: Subject to any disclaimer, the term of this patent is extended or adjusted under 35 U.S.C. 154(b) by 334 days.

(21) Appl. No.: 09/713,558

(22) Filed: Nov. 15, 2000

Related U.S. Application Data

(60) Provisional application No. 60/166,338, filed on Nov. 19, 1999.

(51) Int. Cl.⁷ .............................................. A61B 17/04
(52) U.S. Cl. ....................................................... 606/144
(58) Field of Search .................................... 606/139, 144, 606/145, 147, 148, 149, 222, 223, 232

(56) References Cited

U.S. PATENT DOCUMENTS

| | | | |
|---|---|---|---|
| 2,092,929 A | 9/1937 | Ovington | |
| 4,852,568 A | 8/1989 | Kensey | |
| 4,890,612 A | 1/1990 | Kensey | |
| 4,929,240 A | 5/1990 | Kirsch et al. | |
| 5,342,393 A | 8/1994 | Stack | |
| 5,368,601 A | 11/1994 | Sauer et al. | |
| 5,370,660 A | 12/1994 | Weinstein et al. | |
| 5,383,901 A | 1/1995 | McGregor et al. | |
| 5,405,354 A | 4/1995 | Sarrett | |
| 5,411,520 A | 5/1995 | Nash et al. | |
| 5,417,699 A | 5/1995 | Klein et al. | |
| 5,431,666 A | 7/1995 | Sauer et al. | |
| 5,591,177 A | 1/1997 | Lehrer | |
| 5,669,917 A | 9/1997 | Sauer et al. | |
| 5,766,183 A | 6/1998 | Sauer | |
| 5,810,849 A | 9/1998 | Kontos | |
| 6,056,771 A * | 5/2000 | Proto | 606/222 |
| 6,221,084 B1 * | 4/2001 | Fleenor | 606/148 |
| 6,368,334 B1 * | 4/2002 | Sauer | 606/139 |
| 6,398,796 B2 * | 6/2002 | Levinson | 606/144 |
| 6,436,109 B1 * | 8/2002 | Kontos | 606/148 |
| 6,451,031 B1 * | 9/2002 | Kontos | 606/144 |
| 6,454,777 B1 * | 9/2002 | Green | 606/144 |
| 6,511,489 B2 * | 1/2003 | Field et al. | 606/148 |
| 6,514,263 B1 * | 2/2003 | Stefanchik et al. | 606/144 |

\* cited by examiner

*Primary Examiner*—A. Vanatta
(74) *Attorney, Agent, or Firm*—Cantor Colburn LLP

(57) ABSTRACT

A system is provided for closure of a wound in a patient, such as a puncture hole in a blood vessel, with a suture having a first apparatus for applying a suture capable of closing the wound and a second apparatus for securing a sleeve member over the suture to secure the wound closed. The first apparatus includes a housing, a shaft having first and second ends in which the first end is coupled to the housing, a tissue engaging section coupled to the second end of the shaft, and first and second needles which extend from the housing through the shaft into the tissue engaging section. The tissue engaging section is directed through the wound, and has first and second gaps in which each gap has opposing surfaces into which different sides of the wound can be received. The first needle is extendable into a holder through the first gap to capture one of the two ends of a suture material or thread, and is retractable with the captured suture. The second needle is extendable into another holder through the second gap to capture the opposite end of the suture material, and is retractable with the captured suture. A selecting mechanism enables the selection of the first or second needles. The user operates an actuator member to drive and retract each of the selected needles to retrieve each end of the suture material through the tissue about the wound. After removal of the first apparatus, the suture material is left across the wound, and the second apparatus secures a sleeve member over the two ends of the suture material in proximity of the wound to maintain the wound closed and then cuts the suture material exiting the sleeve member.

90 Claims, 39 Drawing Sheets

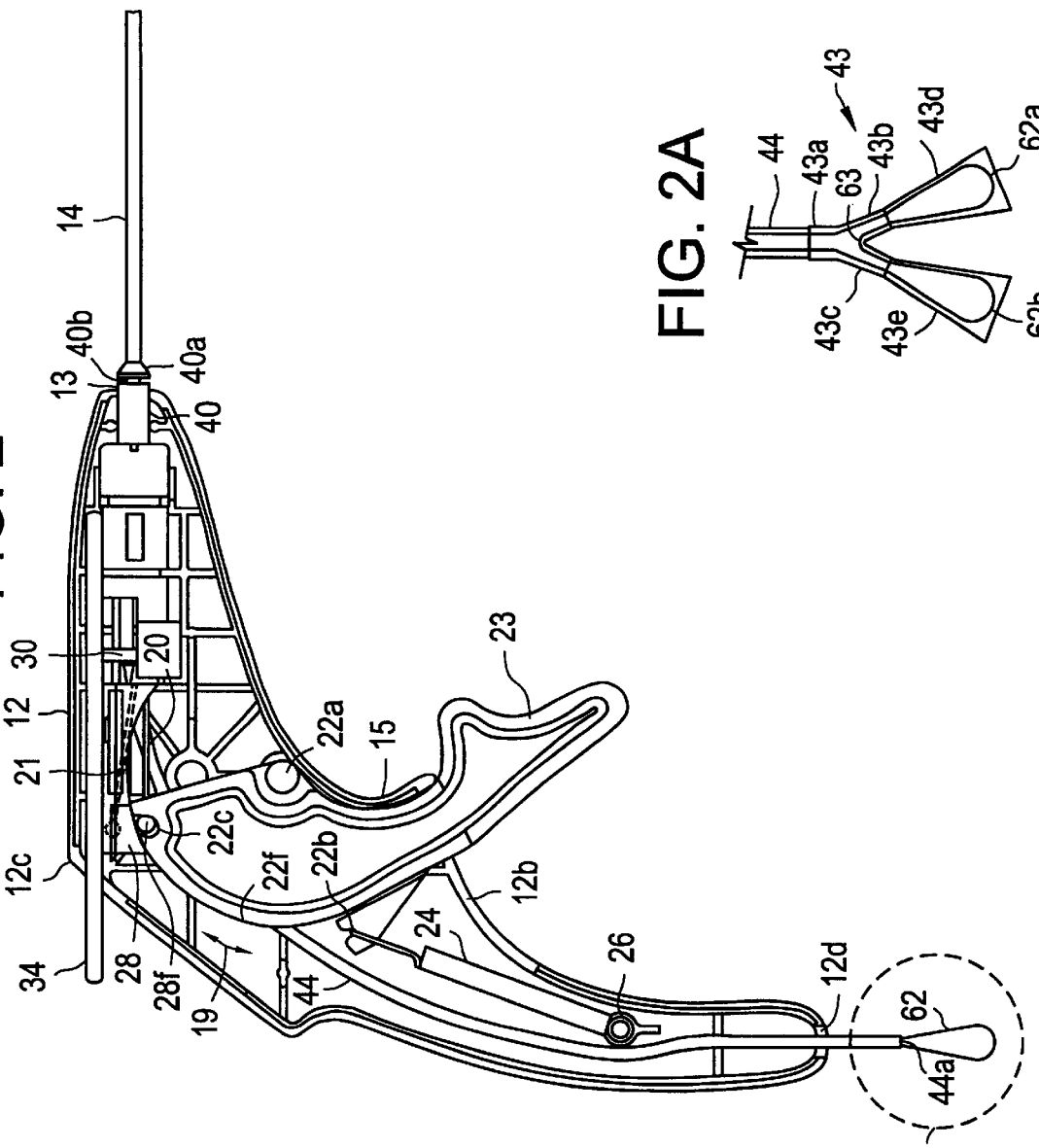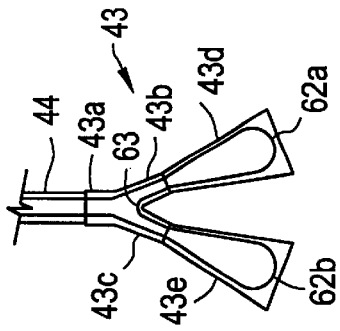

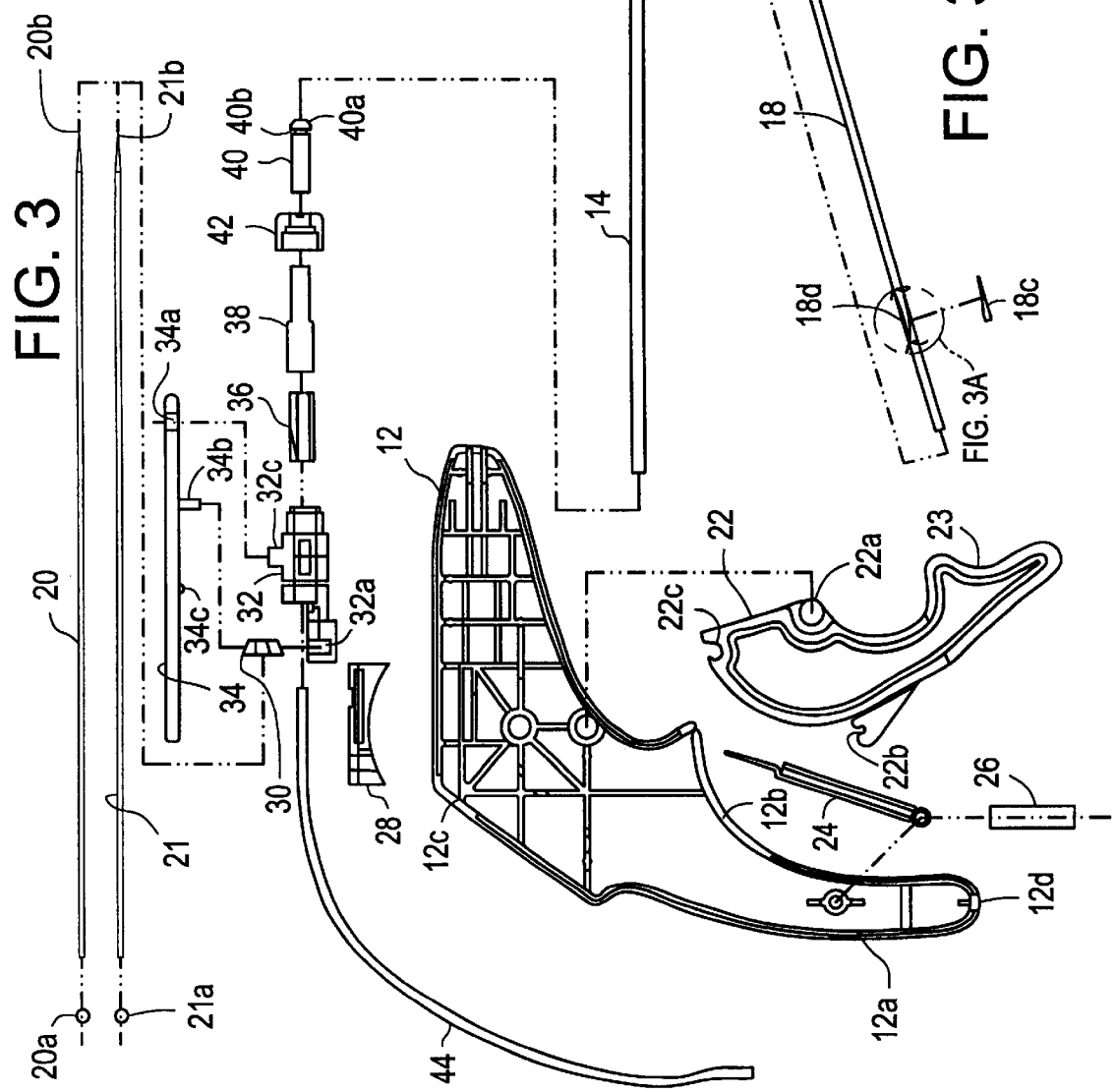

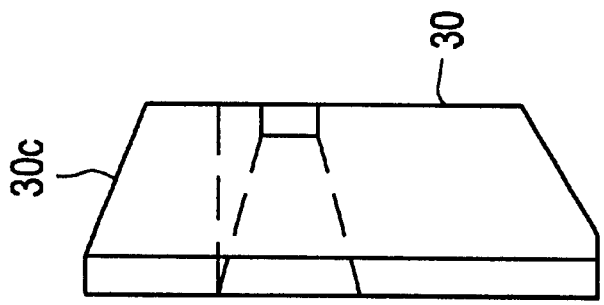
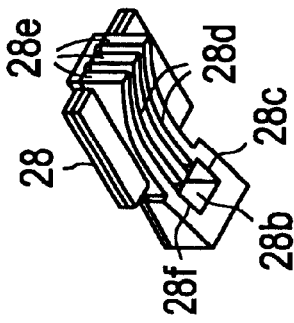
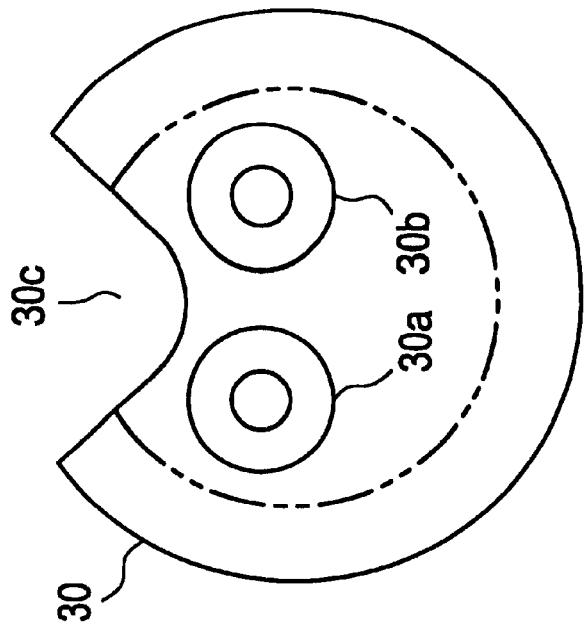

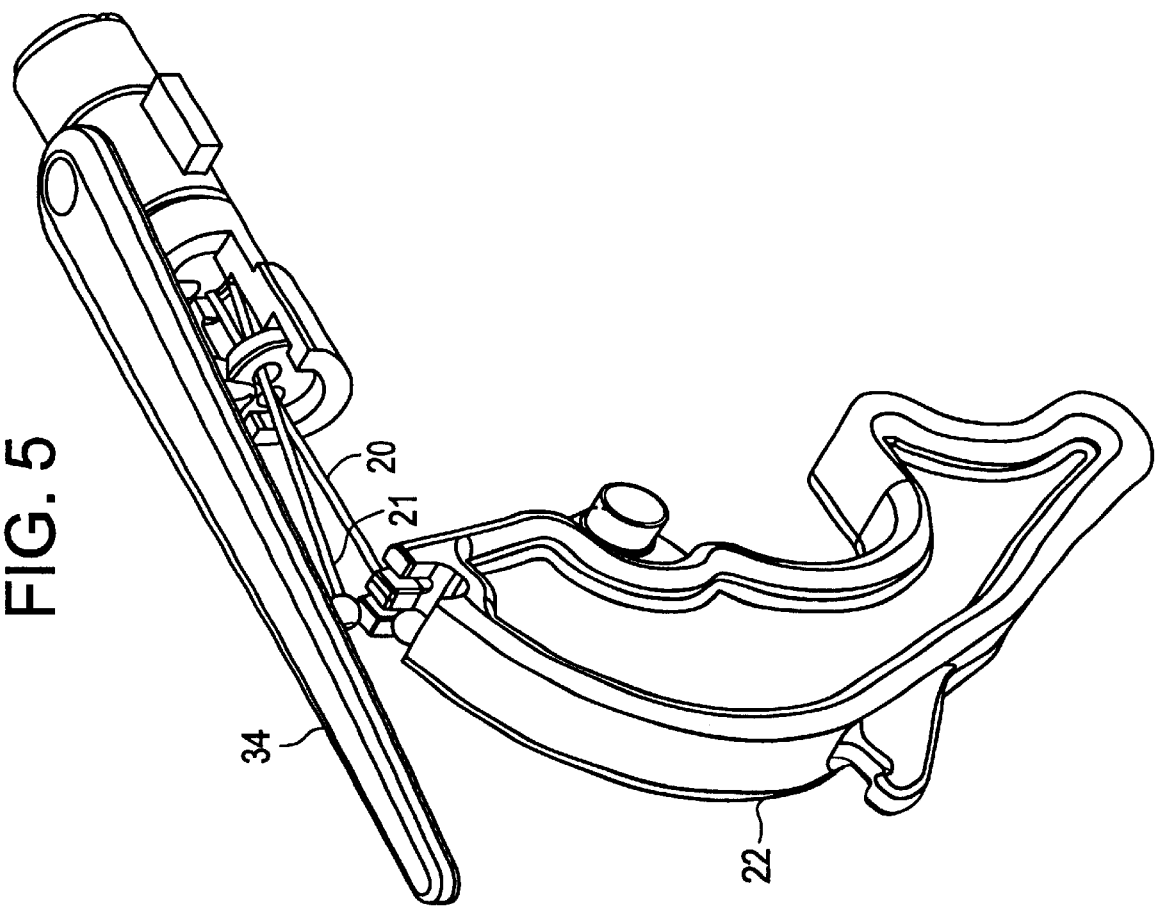

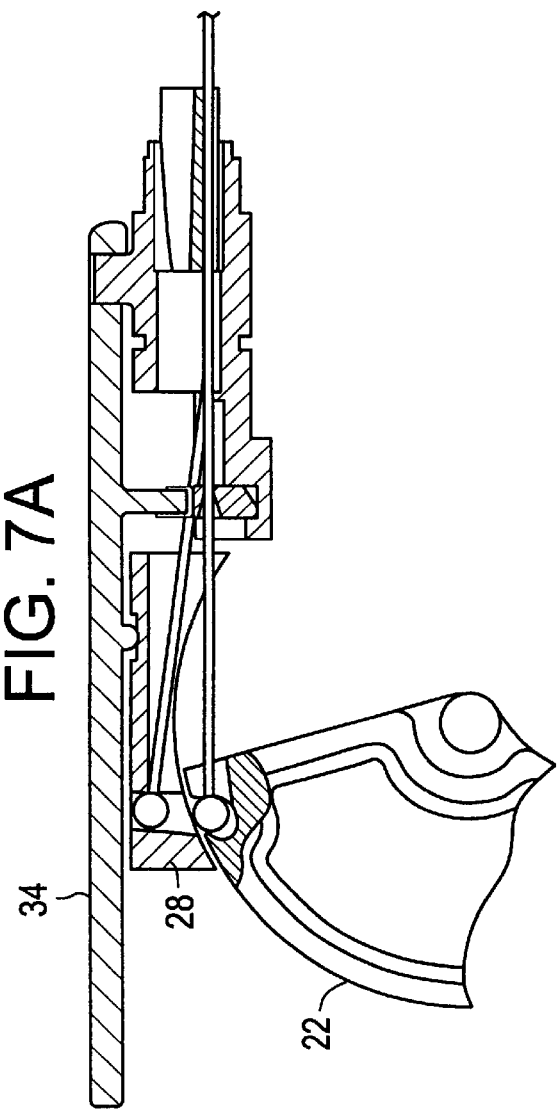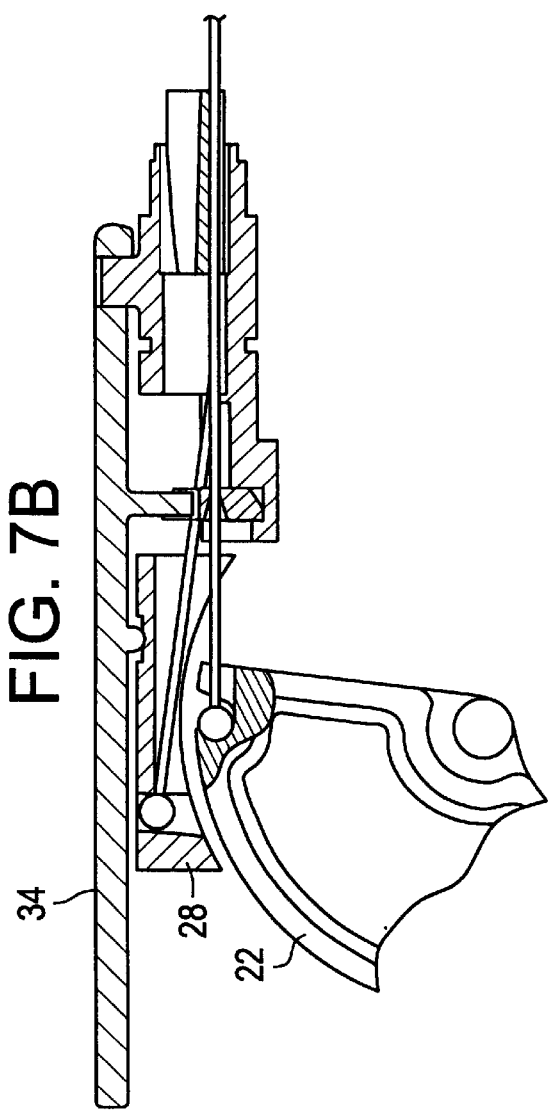

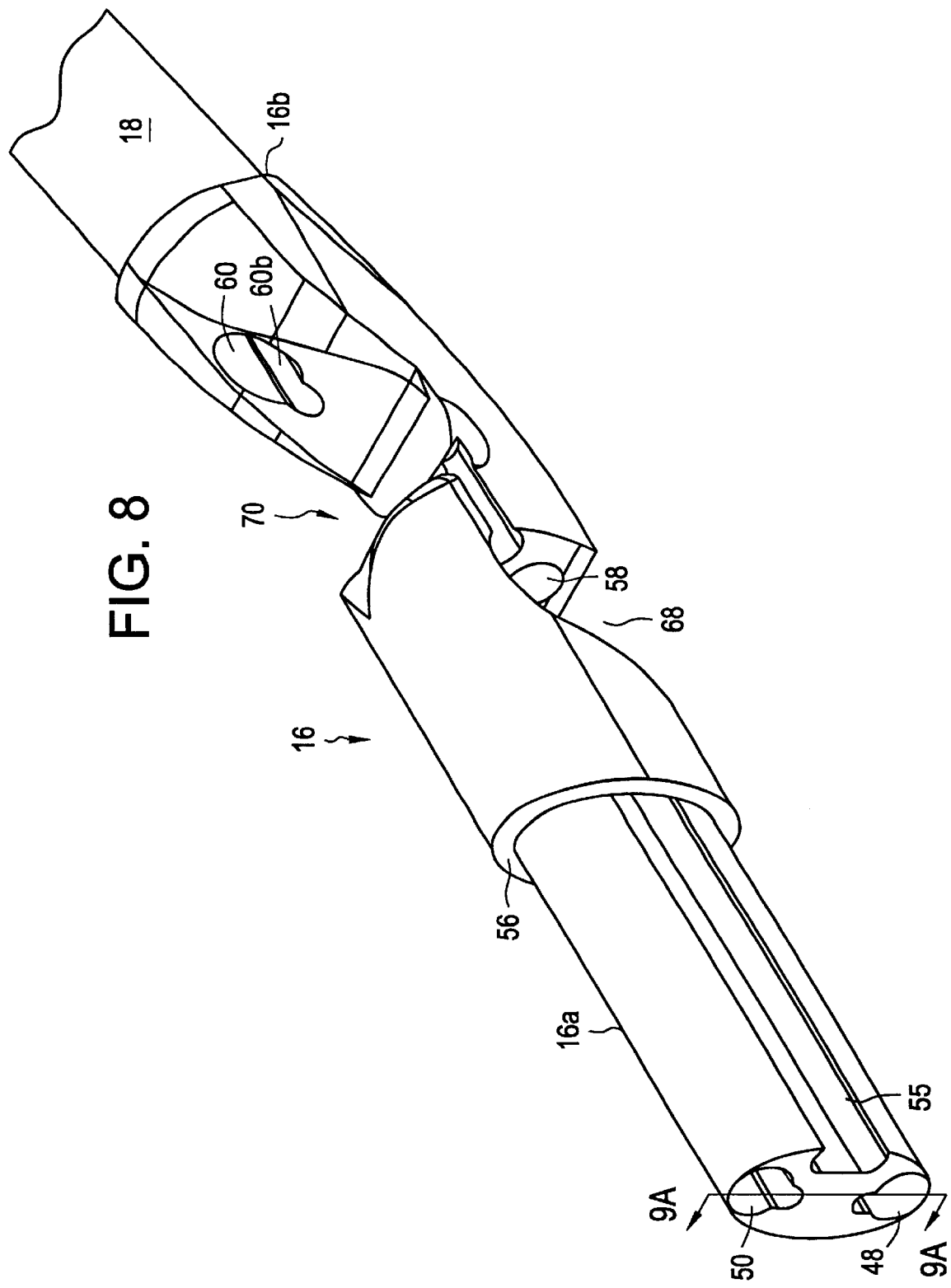

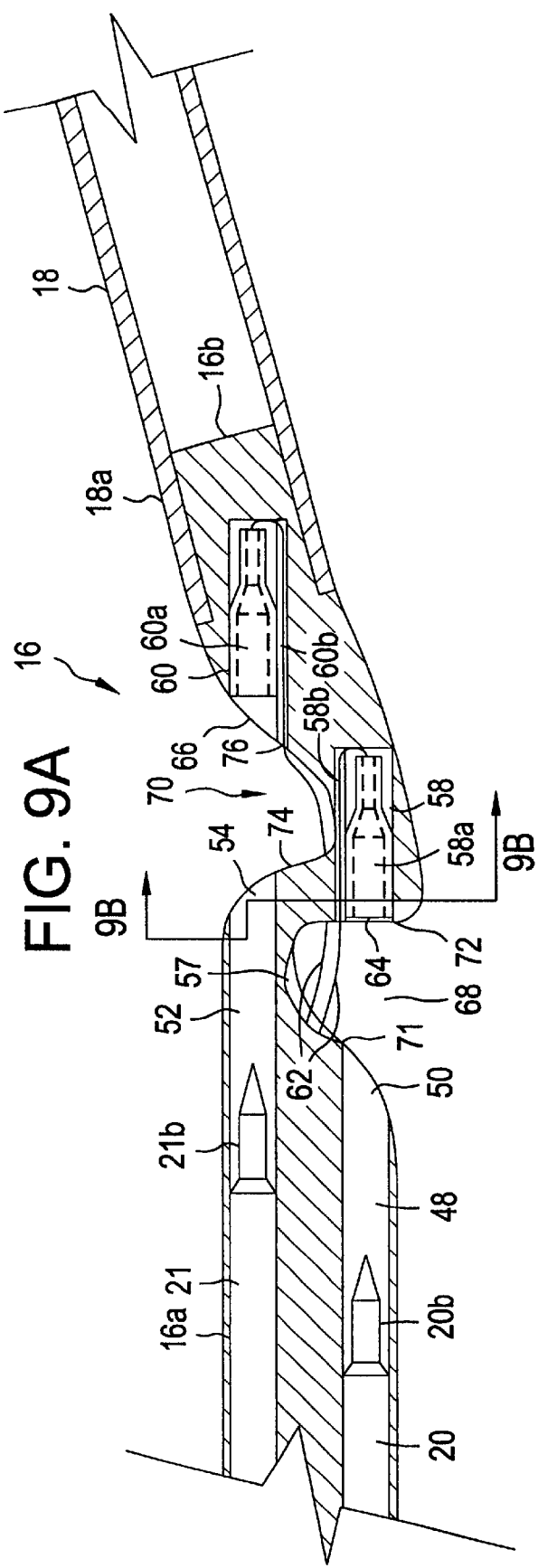
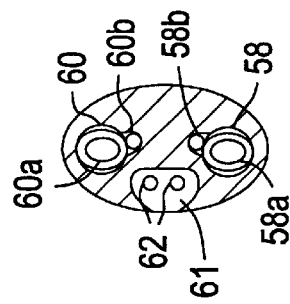

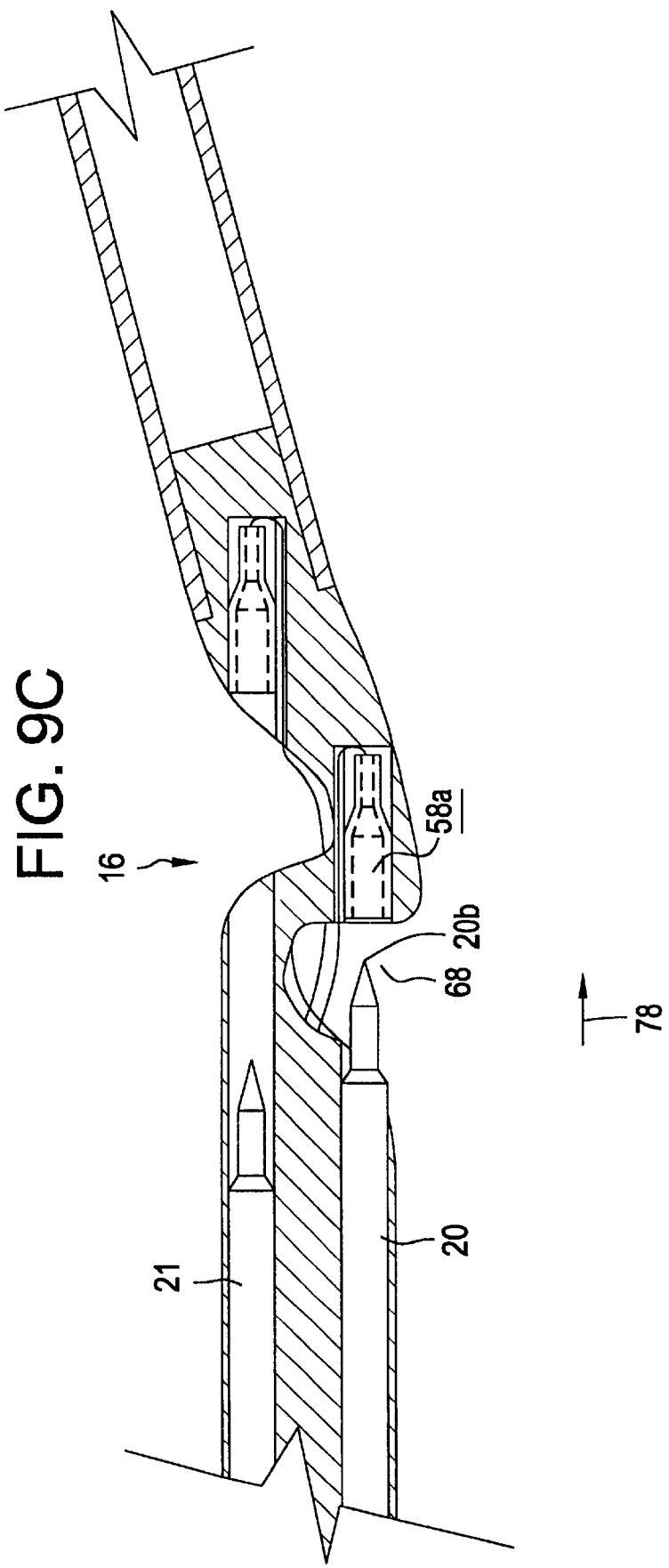

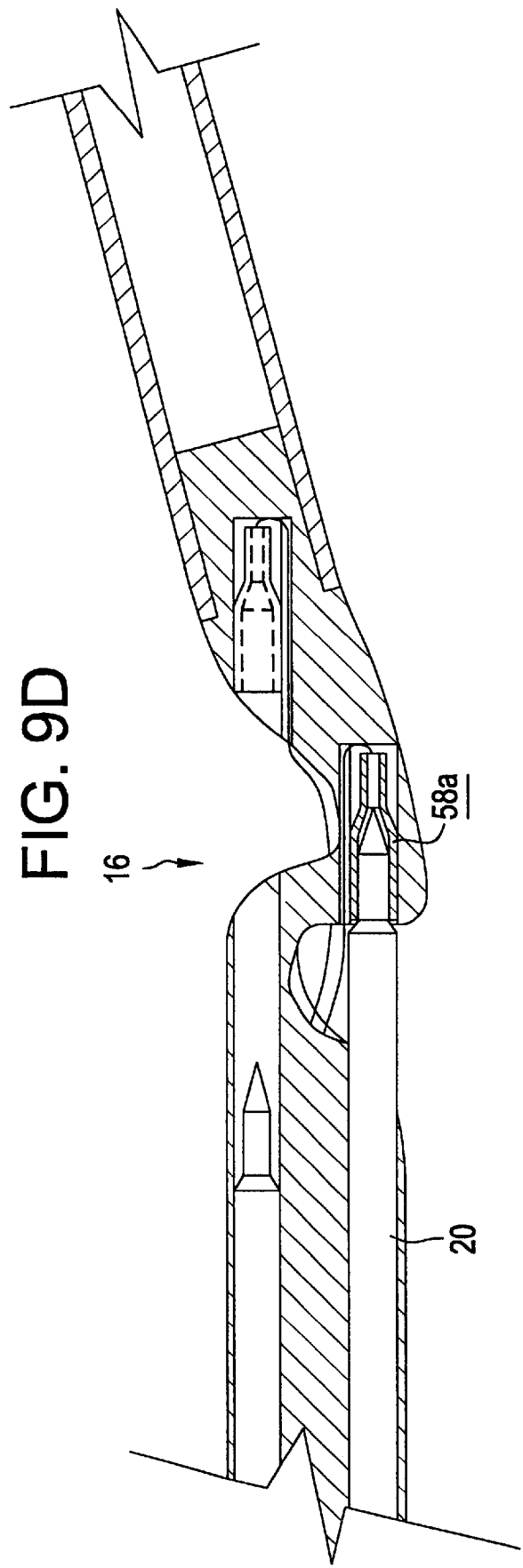

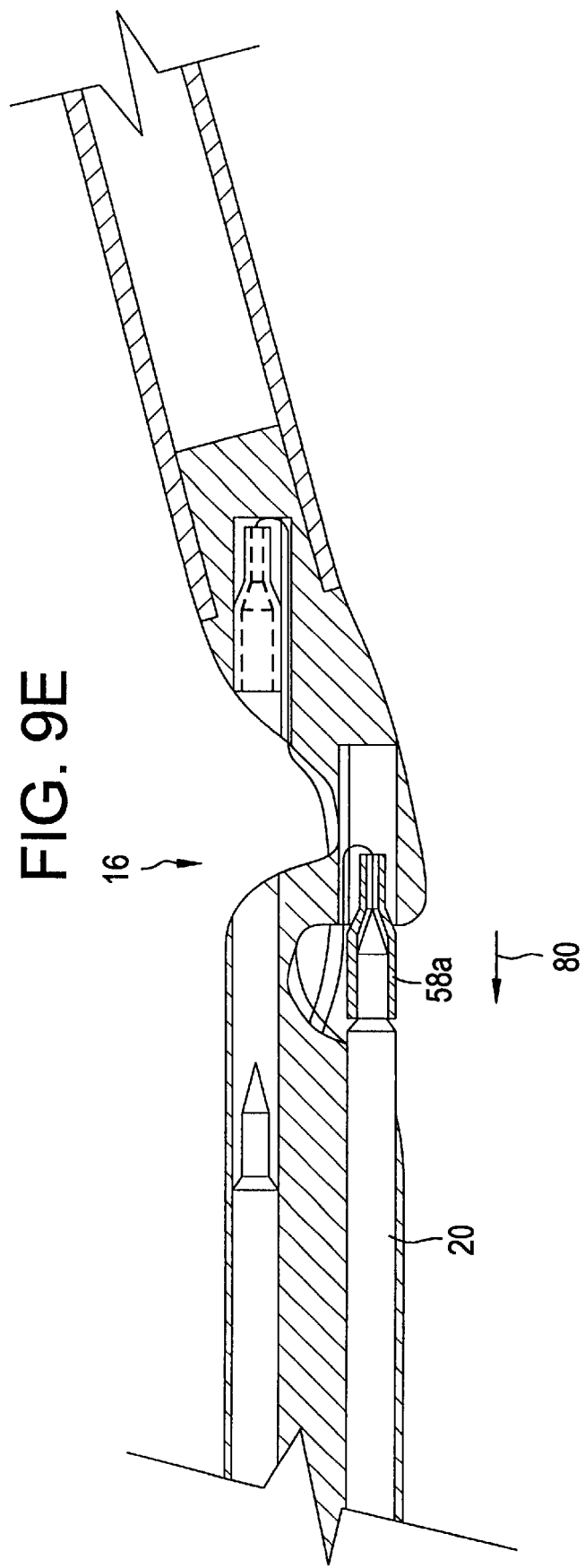

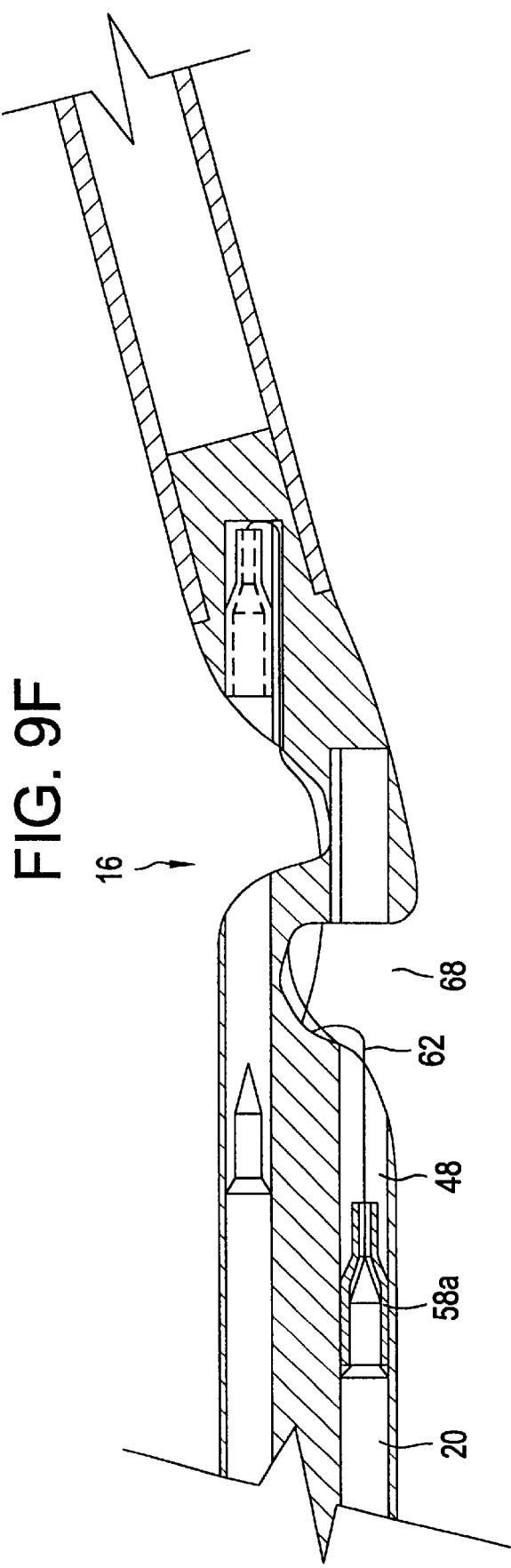

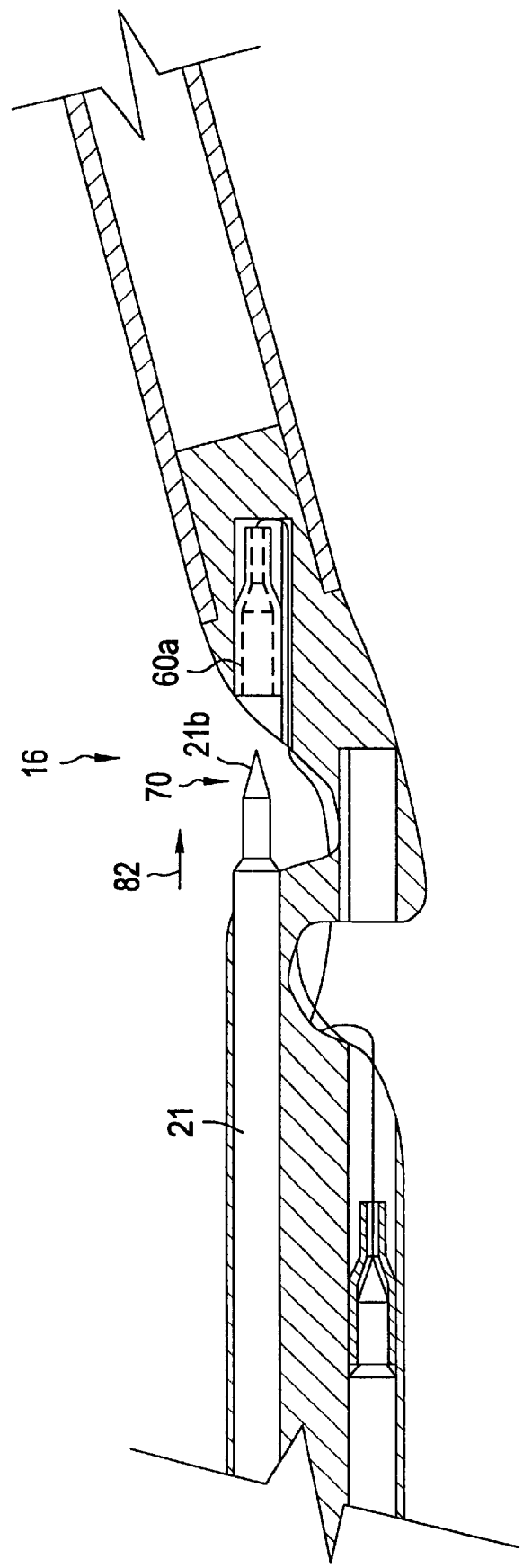

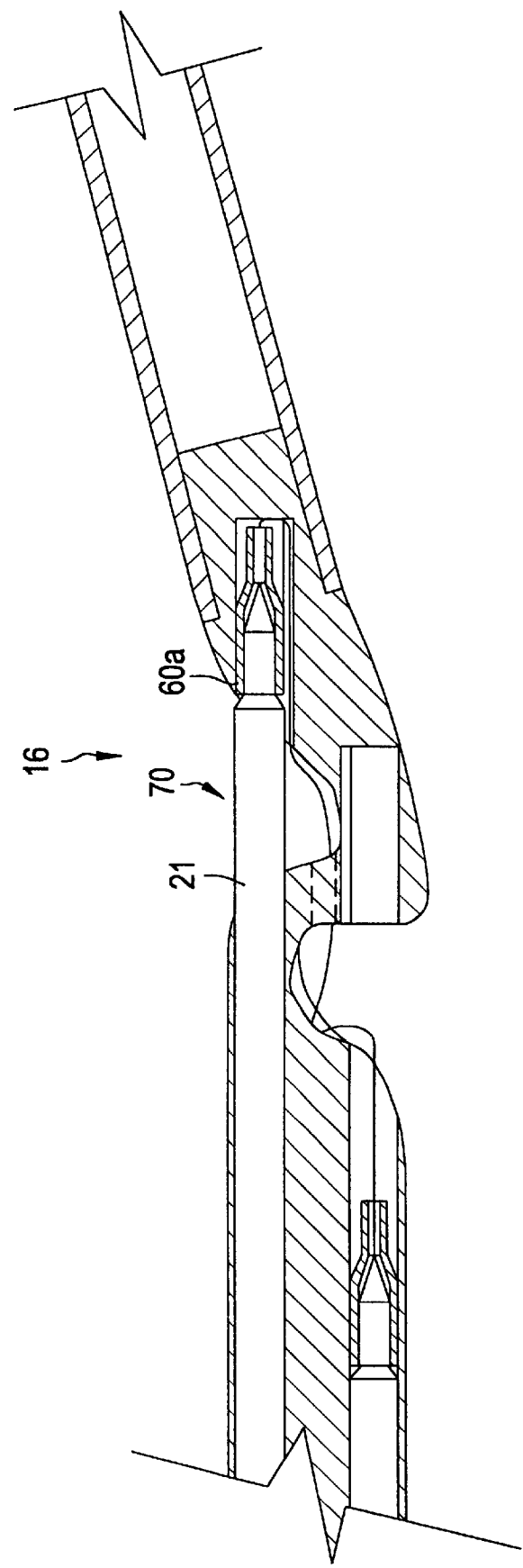

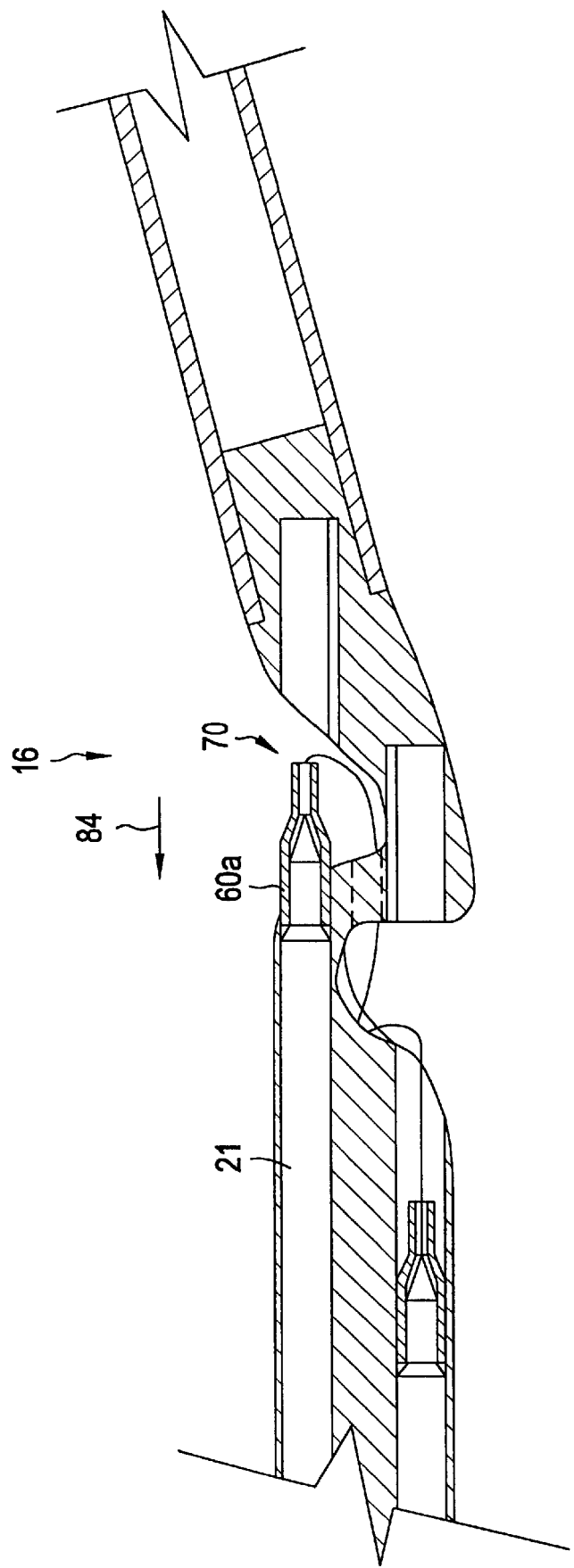

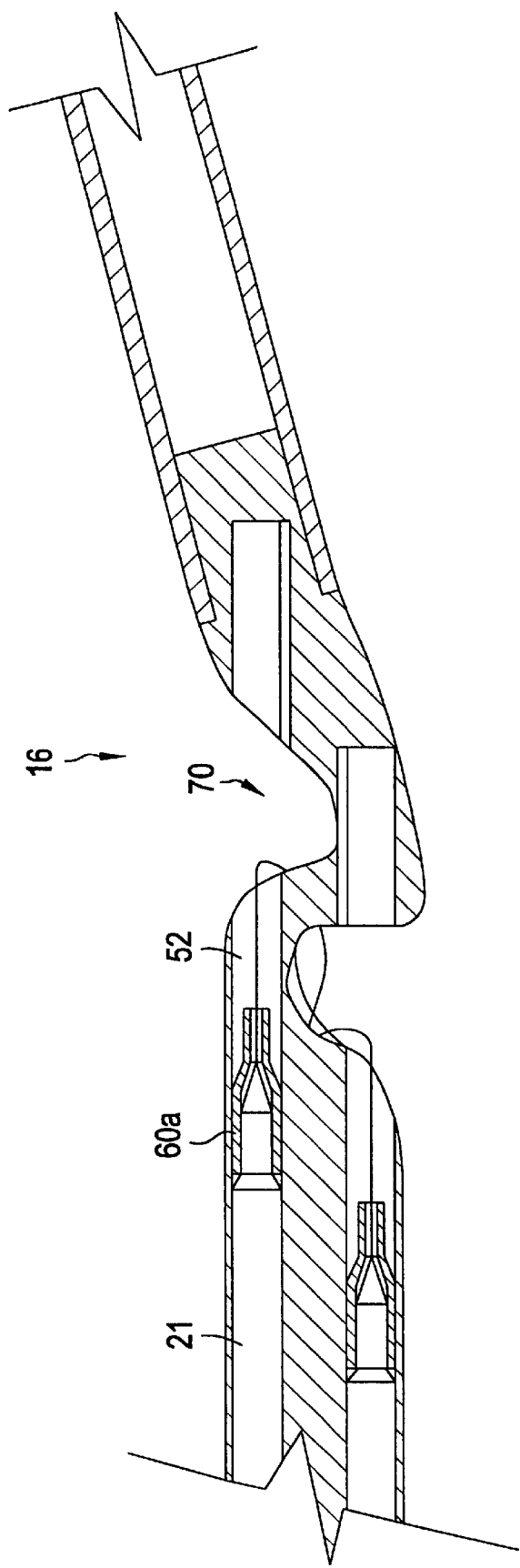

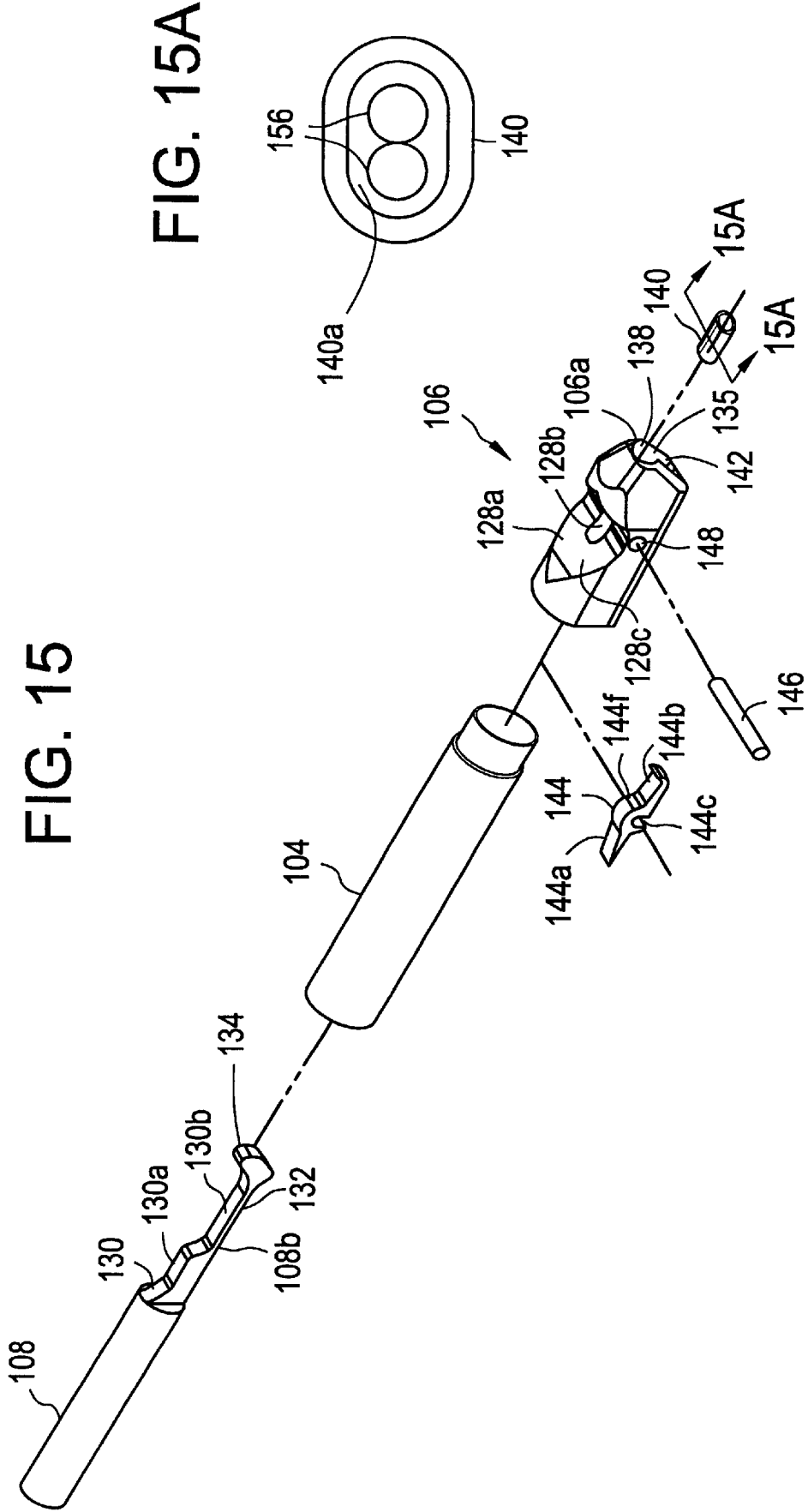

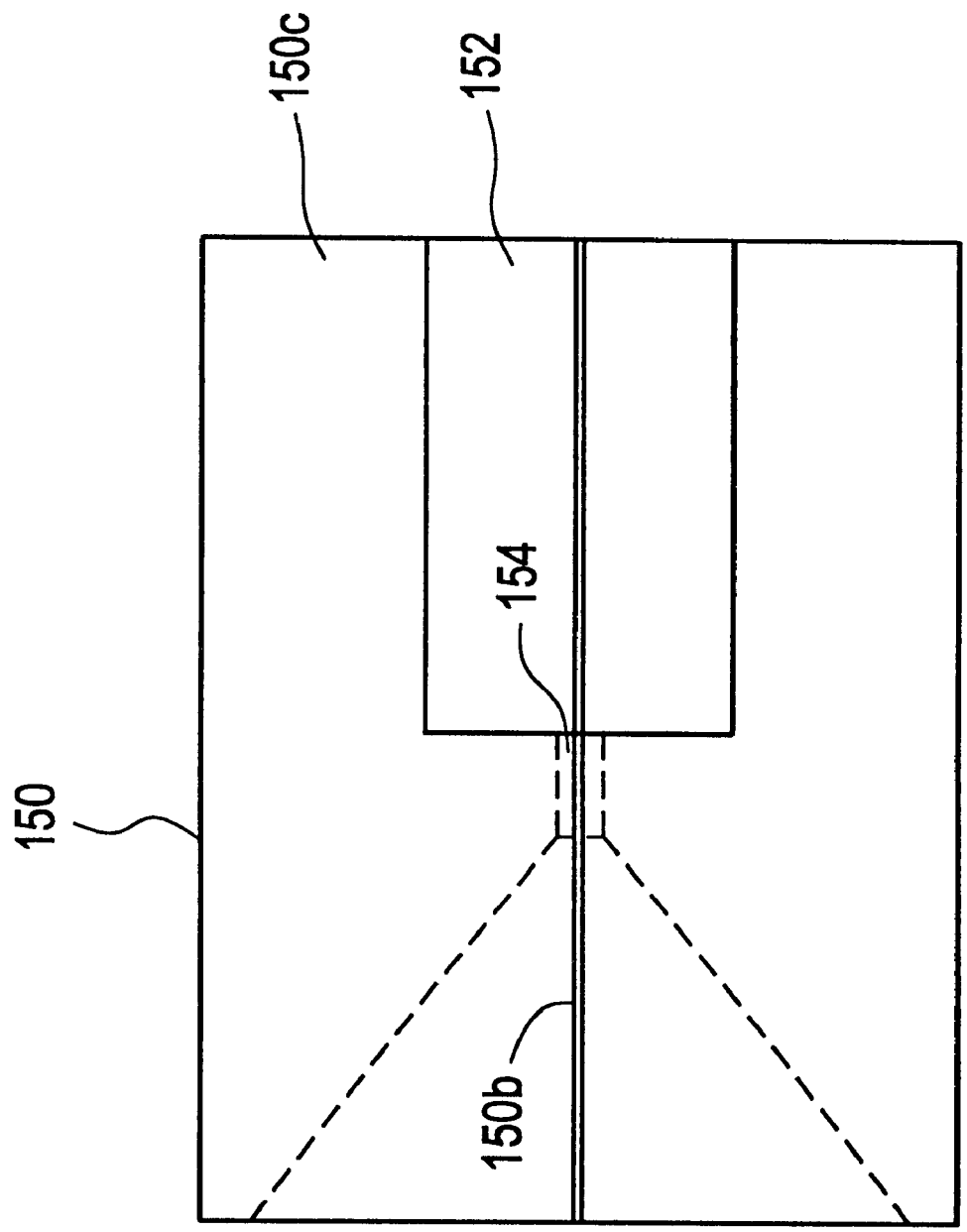

SYSTEM FOR WOUND CLOSURE

CROSS REFERENCE TO RELATED APPLICATIONS

This application is based upon, and claims the benefit of, U.S. Provisional Patent Application No. 60/166,338, filed on Nov. 19, 1999, which is herein incorporated by reference in its entirety.

FIELD OF THE INVENTION

The present invention relates to a system (method and apparatus) for wound closure, and in particular to a system for vascular wound closure utilizing a tissue suturing apparatus and a suture securing apparatus. The invention is suitable for applying at least one suture to close a wound, such as a puncture hole in a blood vessel, after an intravascular catheterization procedure. The invention is also suitable for applying a suture to a wound in other bodily tissue, such as the bowel. The term wound generally refers to herein to a hole, puncture, or any opening in tissue requiring closure.

BACKGROUND OF THE INVENTION

When performing catheterization procedures, such an angiography or angioplasty, a catheter is generally introduced percutaneously (i.e., through the skin) into the vascular system by first penetrating the skin and underlying tissue, and then the blood vessel with a sharpened hollow needle. Location of a blood vessel, such as an artery, is typically achieved by feeling for the pulse, since such structures usually cannot be seen through the skin. Next, a guide wire is commonly inserted through the lumen of the hollow needle and is caused to enter the selected blood vessel. Subsequently, the needle is typically slid off the guide wire and a combination of a dilator and sheath are fed over the guide wire and pushed through the skin to enter the vessel. The guide wire and dilator can then be removed and the desired catheter to carry out the procedure is fed through the lumen of the sheath and advanced through the vascular system until the working end of the catheter is appropriately positioned. Following the conclusion of the catheterization procedure, the working catheter will be withdrawn and, subsequently, the sheath can also be removed from the wound, or left in place to facilitate closure.

At this point in the procedure, the vessel leakage must be controlled in order to stem the flow of blood through the puncture. Because it is common practice to administer a blood thinning agent to the patient prior to many of the catheterization procedures, stemming the blood flow can be troublesome. A common method of sealing the wound is to maintain external pressure over the vessel until the puncture naturally seals. This method of puncture closure typically takes at least thirty minutes, with the length of time usually being substantially greater if the patient is hypertensive or anti-coagulated. In some anti-coagulated patients, the sheath is left in place for hours to allow the anti-coagulant to wear off. When human hand pressure is utilized, it can be uncomfortable for the patient and can use costly professional time on the part of the hospital staff. Other pressure techniques, such as pressure bandages, sandbags or clamps, have been employed, but these devices also require the patient to remain motionless for an extended period of time and the patient must be closely monitored to ensure their effectiveness.

Other devices have been disclosed which plug or otherwise provide an obstruction in the area of the puncture. See, for example, U.S. Pat. Nos. 4,852,568 and 4,890,612, wherein a collagen plug is disposed in the blood vessel opening. When the plug is exposed to body fluids, it swells to create a block for the wound in the vessel wall. A potential problem of plugs introduced into the vessel is that particles may break off and float downstream to the point where they may lodge in a smaller vessel, causing an infarct to occur. Collagen material also acts as a nidus for platelet aggregation and, therefore, can cause intraluminal deposition of hemostatic agent, thereby creating the possibility of a thrombosis at the puncture sight. Other plug-like devices are disclosed, for example, in U.S. Pat. Nos. 5,342,393, 5,370, 660 and 5,411,520.

Surgical clips and clip appliers are known have also been used in vascular surgery, particularly to join severed vessels. For example, U.S. Pat. No. 4,929,240 describes clips generally arcuate in shape, which have two legs that are biased towards each other by clip applier jaws to capture vessel tissue therebetween. While vascular clips have been successfully used in surgery, the surgical procedures in which the clips are typically used allow the surgeon to view the area to be clipped. In catheter puncture repair procedures, however, the wound is generally not visible, making proper clip application, if attempted, difficult.

The use of suturing instruments to close a puncture at the end of a tissue tract is disclosed in U.S. Pat. No. 5,368,601, wherein one of the instruments has a pair of needles, with the tips or points of the needles oriented in a proximal direction, releasably disposed at a distal end thereof. Once in the puncture wound, the instrument is activated to expose the needles. Thereafter, proximal movement of the instrument causes the needles to pass through the wound edge (from the inside to the outside) on either side of the puncture and the needles are withdrawn. A strand of suture material secured between the blunt ends of the needles is also drawn through the needle puncture holes, thereby leaving a span of suture across the hole on the inside of the vessel. The suture can then be tied to close the puncture. A disadvantage to this approach is the potential for needles to deflect in undesirable directions, and the potential difficultly of retrieving the needle tips. Also, the instruments used in this approach are relatively complex, may be unreliable in small sizes, and are costly to manufacture. A similar instrument is also described in U.S. Pat. No. 5,417,699.

Another suturing instrument is described in U.S. Pat. No. 5,431,666 having a pair of longitudinally movable needles to pick up corresponding ends of suture at a distal end of the instrument. A needle capture mechanism provides two needle receiving portions, called ferrules, having a strand of suture material disposed therebetween, which are initially separated from the needles by a single gap in the instrument. In use, tissue to be sutured is disposed in the gap between the needles and the two needle receiving portions called ferrules. A first needle punctures the tissue, engages one end of the suture, and draws it back through the tissue. The instrument can then be relocated to another portion of tissue and the second needle is actuated to pick up and draw the second end of the suture through the tissue. The suture material can then be tied or otherwise cinched in place to secure the tissue closed. In using this instrument, the surgeon is typically able to view the surgical site.

Typically, the user, such as a surgeon or interventional cardiologist, cannot directly view the percutaneous vascular wound that would otherwise facilitate suture placement on opposite sides of the puncture wound. U.S. Pat. No. 5,766, 183 describes a suture instrument for vascular wound closure in which the user does not need to view the wound. The suture instrument has a pair of longitudinally movable needles to pick up corresponding suture ends at a distal end of the instrument. As in U.S. Pat. No. 5,431,666, the strand of suture material can have ferrules at each end. To suture the vascular wound, the instrument is placed through a sheath immediately above vascular wound, or through a tissue tract larger than the vascular wound. One side of the tissue near the wound is punctured by a first needle which engages a ferrule and drawn back through the tissue with the ferrule. The instrument is then rotated to puncture the vascular tissue near another side of the wound with a second needle, which engages the other ferrule and drawn back through the tissue with the other ferrule. After the suture is in place, the instrument is withdrawn leaving the suture behind. Another instrument crimps a sleeve member over the free ends of the suture near the wound and cuts the suture such that the wound is secured closed.

One drawback of the suture instrument of the U.S. Pat. No. 5,766,183 is that since the user does not directly view the site of the vascular wound to be closed, it can be difficult for the user after the first needle punctures the tissue to rotate the instrument such that the second needle is properly aligned at a location which will provide a suture capable of maintaining the wound closed. Preferably, the second needle when applied to the tissue is approximately 180 degrees opposite the location where the first needle punctured the tissue, in respect to the puncture wound along a direction longitudinal with the blood vessel. If the suture is not properly placed across the wound, the suture may not completely close the wound. Another potential problem with this approach is the need for the tissue tract to be larger than the vascular wound.

It is therefore desirable to provide surgical techniques and instrumentation for closing wounds in blood vessels which reliably allows a user without viewing the wound to direct a suture at two locations about the wound which does not need instrument rotation to suture and to facilitate maximizing the distance between the suture and the edges of the wound.

Moreover, improved medical equipment is needed to allow suturing instruments to pass through the sheath already in place in the body of a patient to suture a vascular wound.

SUMMARY OF THE INVENTION

Accordingly, it is the principal object of the present invention to provide an improved system for closure of a wound in a blood vessel that overcomes the drawbacks of the prior art.

Briefly described, the system embodying the invention includes a first apparatus for applying a suture capable of closing the wound and a second apparatus for securing a sleeve member over the suture to secure the wound closed. The first apparatus includes a housing, a shaft having first and second ends in which the first end is coupled to the housing, a tissue engaging section coupled to the second end of the shaft, and first and second needles which extend from the housing through the interior of the shaft into the tissue engaging section, although the needles could be shorter and their movement through the shaft could be assisted by an additional driving mechanism. The shaft and tissue engaging section may be directed to the wound through a sheath (or cannula) previously inserted in the body of the patient. The tissue engaging section has first and second gaps disposed opposite each other. Each gap has opposing surfaces into which different sides of the wound can be received. The first needle is extendable into the first gap through an opening of the tissue engaging section into a needle capturing portion coupled to one of the ends of a suture material, and is retractable with the captured end of the suture material. The second needle is extendable into the second gap through another opening of the tissue engaging section into another needle capturing portion coupled to the other end of the suture material, and is retractable with the captured end of the suture material. A suture tube in the housing extends through the housing and the shaft to the tissue engaging section, and is loaded with loop of suture material having two ends that extend to the needle capturing portions in the tissue engaging section. A selecting mechanism enables automatic or manual selection of each one of the first and second needles. A user operates an actuator member in the housing to drive and retract the selected needle to locate each end of the suture through the tissue about the wound. After removal of the first apparatus, the suture material is left across the wound and the ends of the suture material extend from the sheath. The second apparatus secures a sleeve member over the two ends of the suture material to maintain the wound closed and then cuts the suture material exiting the secured sleeve member.

The first apparatus may further include a tubule flexible guide section coupled to the tissue engaging section to guide the tissue engaging section through the sheath and wound into the blood vessel over a guide wire previously situated therein, and enable the guide wire to be removed. The shaft of the first apparatus may be circular, or oval in cross-section having a major axis of the oval in a first dimension as its extends from the housing, and then oval in cross-section in a second dimension for at least a substantial portion of the shaft near the tissue engaging section to accommodate the two needles being substantially parallel in a first plane near the housing and then substantially parallel in a second plane orthogonal to the first plane near the tissue engaging section. The oval shape of the shaft enables the needles to have a larger distance apart from each other than would otherwise be provided if the shaft were circular in cross-section. The sheath (or cannula) through which the suture instrument is located to access the wound is generally circular in cross-section and made of a flexible material, such that it can deform to accommodate the oval shaft of the suture instrument.

The suture securing instrument of the system includes a tube extending from a housing to a distal end, and a rod extending through the tube in which the rod has first and second ends. The first end of the rod is coupled to a lever pivotally mounted in the housing to move the rod, while the second end of the rod extends into the chamber of the distal end. The distal end has a chamber into which the tube is received, a receptacle at its tip for receiving a round or oval tubular securing sleeve member, and an opening in chamber through which the two ends of suture material can extended after passing through the sleeve member. The second end of the rod is shaped to have an upper surface that is downwardly sloped to provide a step and then terminates at a hammer shaped section at the tip of the distal end. The hammer-shaped section may be adjacent a sleeve member loaded in the receptacle through a slot at the bottom of the receptacle. When a sleeve member is loaded in the receptacle, the user may pull the lever to retract the rod which enables the hammer-shaped section of the rod to be raised by a ramp located at the bottom of the chamber of the distal end, such that the pressure applied upon the sleeve member by the hammer-shaped section crimps at least part of the sleeve member. A knife is pivotally mounted in the chamber of the distal end, and, responsive to the hammer-shaped section of the rod abutting the knife as the rod is further retracted, rotates the knife upwards to cut the suture material extending from the crimped sleeve member. The suture securing instrument may then be withdrawn through the cannula leaving the crimped sleeve member to maintain the wound closure by the suture.

The invention further includes a method for using the first and second apparatuses to close a vascular wound, and a surgical kit including both the first and second apparatuses as parts of the kit.

One advantage of first apparatus is that it allows a suture to be placed through a sheath and thus, there is no need to expand the diameter of the a puncture wound in order to place a suture across the wound, such as often needed in prior art suturing techniques. A further advantage of the first apparatus is the ability to locate the edges of the wound to be sutured from inside a blood vessel.

BRIEF DESCRIPTION OF THE DRAWINGS

The foregoing objects, features and advantages of the invention will become more apparent from a reading of the following description in connection with the accompanying drawings, in which:

FIG. 2 is a partial side view of the tissue suturing apparatus of FIG. 1 in which the right cover of the housing of the apparatus is removed;

FIG. 2A shows an extension member for the suture tube of the tissue suturing apparatus of FIG. 2;

FIG. 3 is an exploded view of the tissue suturing apparatus of FIG. 1 in which the right cover of the housing is removed;

FIG. 3A is a partial view of the guide section of the tissue suturing apparatus of FIG. 3;

FIG. 4A is another perspective view of the retainer member of FIG. 4;

FIGS. 4B and 4C are front and side views of the cam member of FIG. 4;

FIG. 5 is a right perspective view of the needle selection mechanism in the tissue suturing apparatus of FIG. 1 showing the needle selector lever in a left position;

FIG. 7A is a partial cross-sectional view of the needle selection mechanism and the actuator member of the apparatus of FIG. 1 showing the ends of the two needles in which one needle is positioned downwards to be driven by the actuator member and the other needle is positioned upwards in the needle retainer member;

FIG. 7B is another partial cross-sectional view of the needle selection mechanism of the apparatus of FIG. 1 in which one of needles of FIG. 7A is being driven forward;

FIG. 8 is a perspective view of the tissue engaging section of the apparatus of FIG. 1;

FIG. 9A is a cross-sectional view of the tissue engaging section along lines 9A—9A of FIG. 8 in which ferrules have been loaded into ferrule holders;

FIG. 9B is a cross-sectional view of the tissue engaging section along lines 9B—9B of FIG. 9A when loaded with ferrules;

FIGS. 9C–9F are cross-sectional views of the tissue engaging section along lines 9A—9A of FIG. 8 showing one of the needles capturing a ferrule;

FIGS. 10A–10D are cross-sectional views of the tissue engaging section along lines 9A—9A of FIG. 8 showing another one of the needles capturing a ferrule;

FIG. 11A is a perspective view of the distal end of the suture securing apparatus of FIG. 11 showing the top and right side of the distal end;

FIG. 13A is an expanded view of the distal end of the suture securing apparatus of FIG. 13;

FIG. 15 is an exploded perspective view of the distal end of the suture securing apparatus of FIG. 13;

FIG. 15A is a cross-sectional view of the sleeve member along lines 15A—15A of FIG. 15;

FIG. 16G is a top view of the attachment to aid loading of two ends of suture material into the suture securing apparatus of FIG. 16C;

DETAILED DESCRIPTION OF THE PREFERRED EMBODIMENTS

Figure 1:
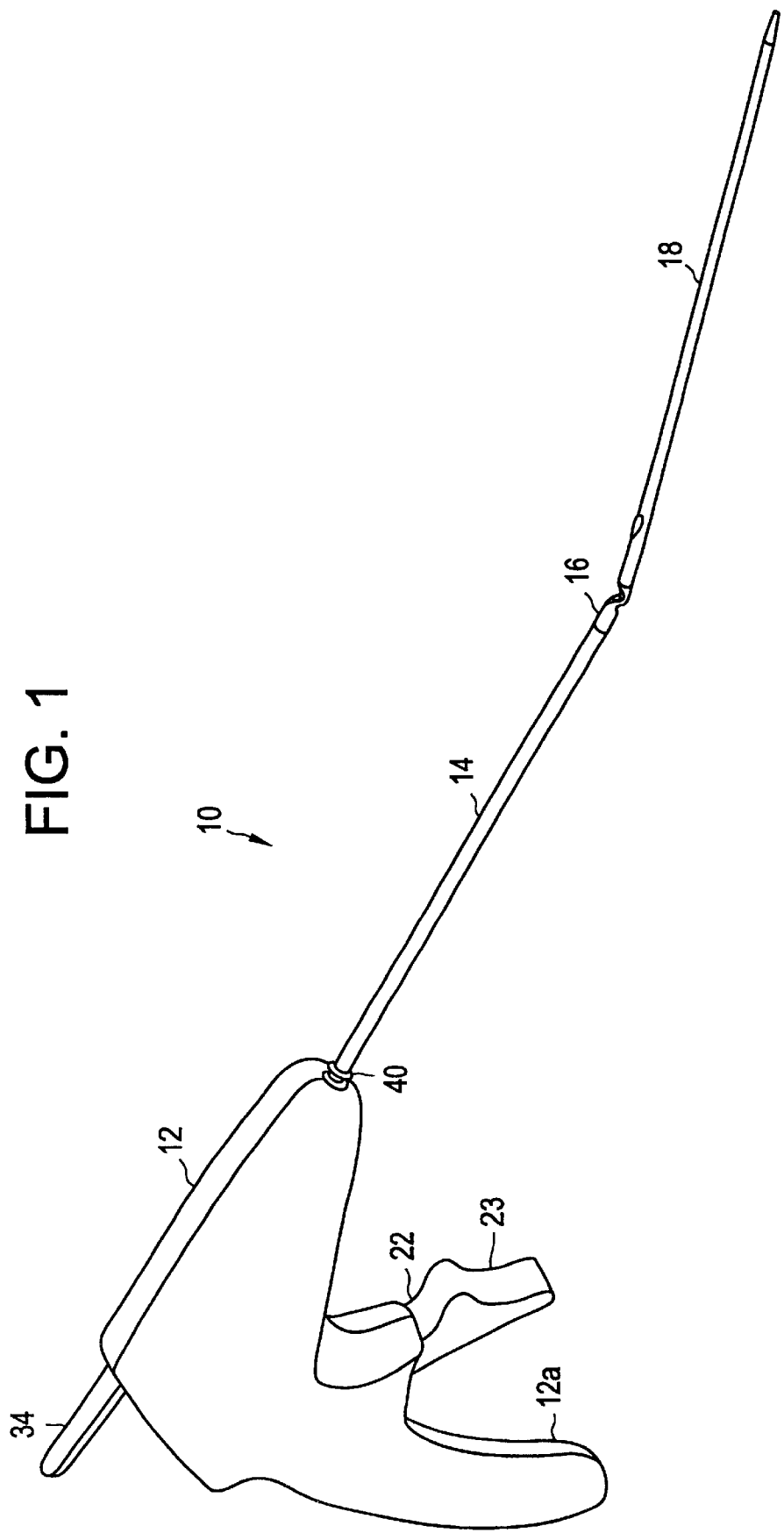
FIG. 1 is a perspective view of the tissue suturing apparatus in accordance with the present invention.
Figure 4:
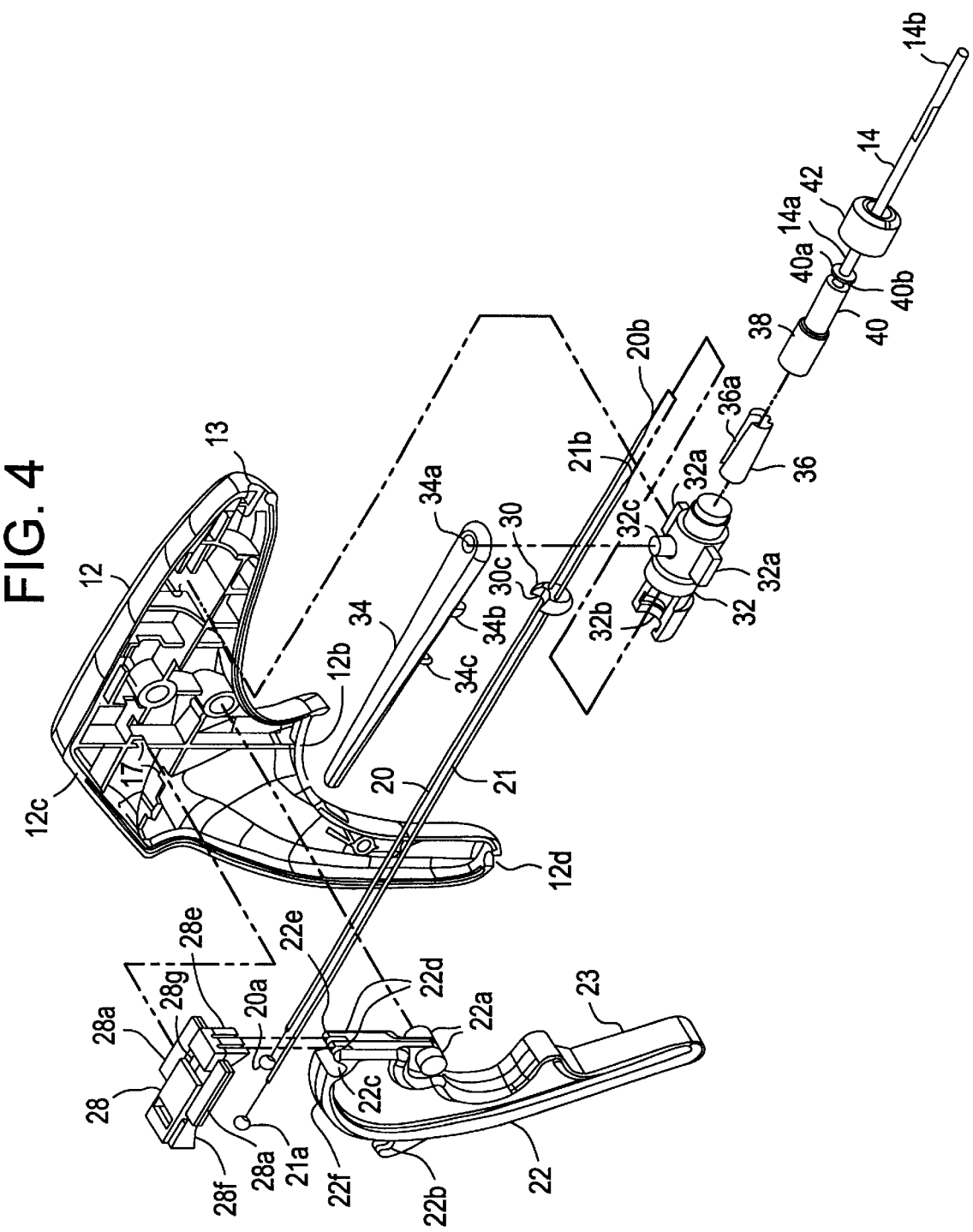
FIG. 4 is an exploded perspective view of the tissue suturing apparatus of FIG. 1 in which the right cover of the housing is removed.

Referring to the drawings, wherein like reference numerals identify similar or identical elements throughout the several views, an apparatus for applying a suture to body tissue is illustrated in FIGS. 1–10D and is designated generally by reference numeral 10. Another apparatus is also disclosed, designated by reference numeral 100 and illustrated in FIGS. 11–16F, for applying a connecting sleeve around the suture after it has been applied to the body tissue by apparatus 10 in order to secure the suture. Note that the terms "first" and "second" as used herein are for the reader's convenience and should not be interpreted as necessarily denoting the order in which the components are actuated. The system for wound closure of the present invention encompasses the combination of apparatuses 10 and 100.

Referring to FIGS. 1–4, apparatus 10 is shown having a housing 12, a tissue engaging section 16, a shaft 14 extending from an opening 13 in the housing to the tissue engaging section 16, and a flexible guide tube 18 coupled to the tissue engaging section 16. The housing 12 has a body shaped like a pistol having a handle portion 12a, and may be made of a two-piece construction of molded plastic. The apparatus 10 includes a pair of needles 20 and 21, which extend from housing 12 through the shaft 14 into the tissue engaging section 16. Each needle 20 and 21 has a non-tissue engaging end in the housing having a spherical member 20a and 21a, such as a ball or bearing, respectively, attached thereto. Both needles 20 and 21 and spherical members 20a and 21a may be a made of metal, such as surgical stainless steel. The spherical member 20a and 21a may have a bore into which the non-tissue engaging ends of the needles 20 and 21, respectively, extend and joined thereto, such as by welding.

The apparatus 10 includes an actuator member 22 having two pins 22a extending into holes in the sides of housing 12 upon which the actuator member is pivotally mounted in the housing. Actuator member 22 has a portion which extends through an opening 12b in housing 12 to provide a trigger 23. A coil spring 24 is provided which hooks at one end in a notch 22b of actuator member 22 and is wound at the other end around a pin 26 located in holes in the sides of housing 12, such that the actuator member 22 is spring biased to retain trigger 23 normally in a forward position, as shown for example in FIG. 2. The body of housing 12 has a front portion 15 providing a stop that limits the pivotal movement of the actuator member 22 to define the forward position of the trigger 23. A notch 22c is provided in the actuator member 22 which is shaped to received one of the non-engaging ends of needles 20 or 21, i.e., spherical members 20a or 21a, to be driven forward by the actuator member 22 by a user pulling the trigger 23 portion of actuator member 22 towards handle portion 12a. Two grooves 22d are provided by three fingers 22e into which the needle 20 or 21 near the spherical members 20a or 21a, respectively, may lie.

A retainer member 28 is fixed in housing 12 by two flanges 28a above actuator member 22. As best shown in FIG. 4A, the retainer member 28 has a chamber 28b having a lower opening 28c and two grooves 28d formed by fingers 28e which allow the spherical members 20a or 21a of needles 20 or 21, respectively, to be received in chamber 28b to restrict movement of the needle when held therein. The lower surface 28f of retainer member 28 is curved and faces correspondingly curved upper surface 22f of actuator member 22, such that the actuator member 22 is slidable along lower surface 28f responsive to a user pulling and releasing trigger 23.

Figure 6:
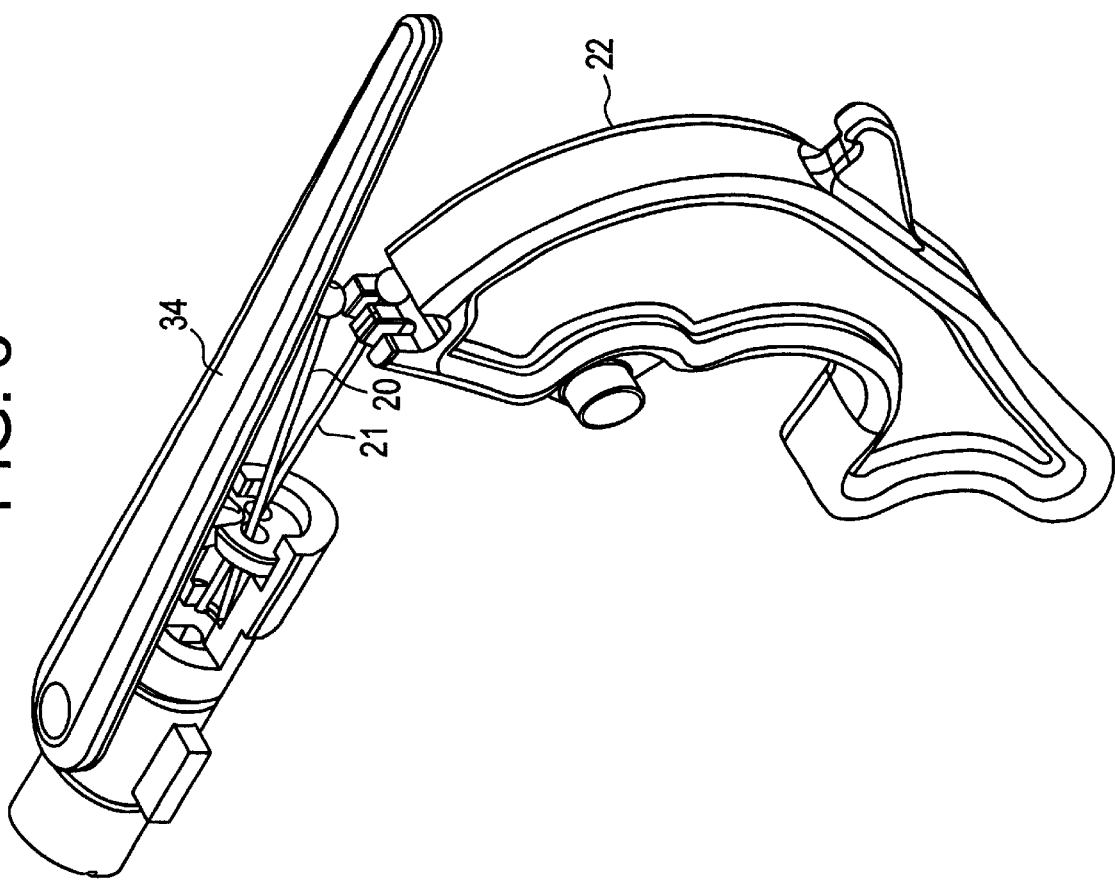
FIG. 6 is a left perspective view of the needle selection mechanism in the tissue suturing apparatus of FIG. 1 showing the needle selector lever in a right position.

To select which of the needles 20 and 21 is to be driven by actuator member 21, apparatus 10 has a needle selection mechanism having a selector lever (or arm) 34 which is rotationally coupled with a cam member 30. The cam member 30 and selector lever 34 is supported by an adapter 32 in housing 12. Adapter 32 is mounted in housing 12 by two flanges 32a. The selector lever 34 is pivotally mounted by a pin 32c extending upwards from adapter 32 at a hole 34a through the lever. Selector lever 34 extends through an opening 12c in housing 12 and has a downwardly protruding member 34b which is received in a notch 30c of cam member 30 to rotate cam member 30 in a pocket 32b in the adapter 32 as the selector lever is moved left or right. The cam member 30 has a tapered surface 30c to facilitate its rotation in pocket 32b and two tapered apertures 30a and 30b through which needles 20 and 21 respectively extend, as best shown in FIGS. 4B and 4C. To select needle 20 to be driven, the selector 34 is moved left which rotates the cam member 30 to position needle 20 down and needle 21 up, such that end 20a is located in notch 20c and end 21a is located in retainer member 28 (FIG. 5). To select needle 21 to be driven, the selector 34 is moved right which rotates the cam member 30 to position needle up and needle 21 down, such that end 21a is located in notch 20c and end 20a is located in retainer member 28 (FIGS. 6 and 7A). FIG. 7B shows the forward movement of actuator member 22 to drive needle 21 as needle 20 is retained in the needle retainer member 28.

The needle selector 34 may further have another downwardly protruding member 34c which rides in a slot 28g on the upper surface of retainer member 28. The slot 28g is contoured to have angled lower regions on either side of a raised region into which member 34c can be located to releasably lock the position of lever 34 left or right.

The adapter 32 has a bore extending therethrough in which a needle spreader 36 is located. Needle spreader has two channels into which needles 20 and 21 are respectively located to increase the distance between the needles 20 and 21 as they extend toward cam member 30, such that the needles are properly aligned to apertures 30a and 30b in the cam member.

Figure 17A:
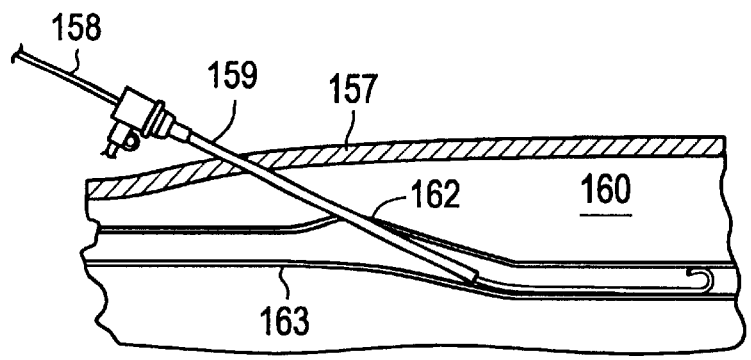
FIGS. 17A–17M show an example of the procedure for using the tissue suturing apparatus of FIG. 1 and the suture securing apparatus of FIG. 11 to close a wound in a blood vessel.

The shaft 14 is mounted to housing 12 by a shaft mount 38 which is D-shaped at one end to register into a corresponding shaped opening in the adapter 32, an extending member 40 into which the shaft 14 is received, and a threaded nut 42 having an opening which extends over the shaft 14, extending member 40 and shaft mount 38, and screws onto the end of the adapter 32 to secure the shaft 14 to housing 12. Shaft 14 may be made of extruded plastic, or other substantially rigid material. Extending member 40 has a tapered annular portion 40a and a gap 40b onto which a sheath 159 (such as shown in FIG. 17A) can be inserted to releasably attach the sheath to apparatus 10 when the shaft 14, tissue engaging section 16, and guide section 18 is passed through the sheath. For example, such a sheath may be part of a percutaneous catheter introducer set sold by C. R. Bard Ireland Limited of Galway, Ireland. Sheath 159 has a head 159a having an opening capable of receiving the extending member 40, such when the extending member is inserted into the sheath, a gasket within the opening of head 159a registers into gap 40b and held in place by tapered annual portion 40a. The apparatus 10 may be released from sheath 159 by pulling the sheath away from housing 12. The tapered annular portion 40a may be made of a rigid material capable of sufficient elasticity to pass through the gasket in the sheath 159, and is shaped and sized in accordance with the opening of head 159a. In addition to releasably attaching housing 12 to a sheath, the housing may also be releasably attached to a catheter.

Apparatus 10 has a suture tube 44 which extends through an opening 12d in the handle portion 12a of housing 12, through notches 17 (FIG. 4) along the interior of the left side of housing 12, a groove 36a in needle spreader 36 (FIG. 4), and through shaft 14 to tissue engaging section 16. When a strand of suture material is loaded through tube 44, as shown in FIG. 2, the suture material 62 extends in a loop through the tube 44 in which the two ends of the suture material are located in the tissue engaging section 16. For example, the suture material may represent monofilament suture material or braided suture material. The suture tube 44 may have an optional extension member 43 coupled to the end 44a of the suture tube, as shown in FIG. 2A. The extension member 43 has a splitter 43a which forks to split tube 44 into two tubes 43b and 43c. Each of the tubes 43b and 43c may then be coupled to a separate compartment provided by hollow transparent member 43d and 43e, respectively. When a strand of suture material is loaded through tube 44 and extension member 43, the suture material has a midpoint 63 between its two ends in splitter 43a, the loop 62 is divided into two loops 62a and 62b drawn through each of transparent members 43d and 43e through tubes 43b and 43c, respectively. Thus, loop 62a is closer to one of the ends of the suture material, and loop 62b is closer to the other end of the suture material. The transparent members 43d and 43e are optional, but can be used to protect each loop of suture material therein. The end of each transparent member 43d and 43e may be open or closed. The extension member 43 provides the user of apparatus 10 with a status indicator for the deployment of the suture. In other words, the user can visualize the suture material associated with loop 62a or 62b, respectively, when each end of the suture material is drawn up through suture tube 44 as each needle 20 and 21, respectively, places one end of the suture material through tissue.

Figure 7D:
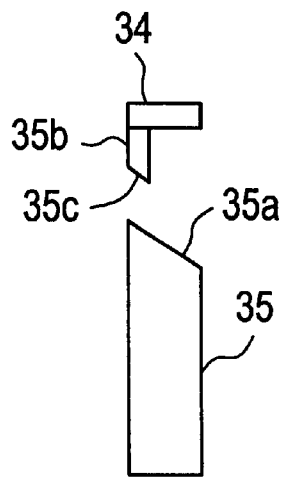
FIG. 7D is a partial side view of the embodiment of the needle selection mechanism of FIG. 7C.
Figure 7C:
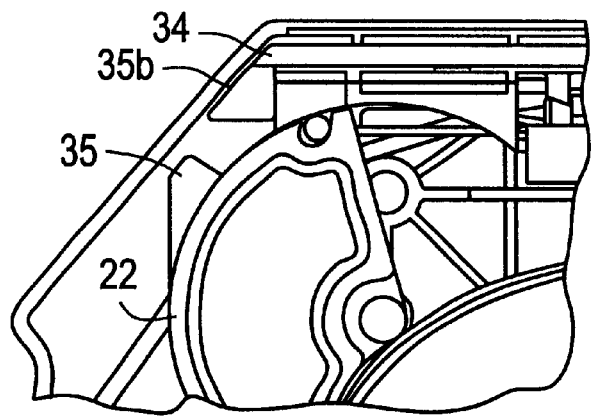
FIG. 7C is another partial cross-sectional view showing an embodiment of the needle selection mechanism of the apparatus of FIG. 1 in which the needles are automatically selected.
Figure 7F:
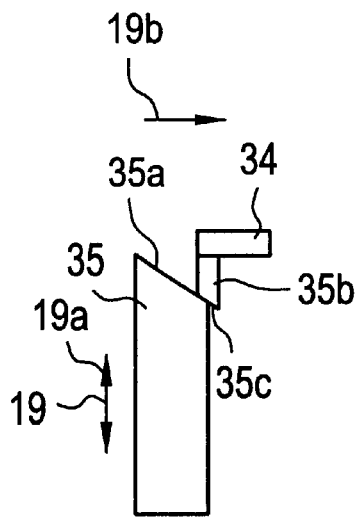
FIG. 7F is a partial side view of the embodiment of the needle selection mechanism of FIG. 7E.
Figure 7E:
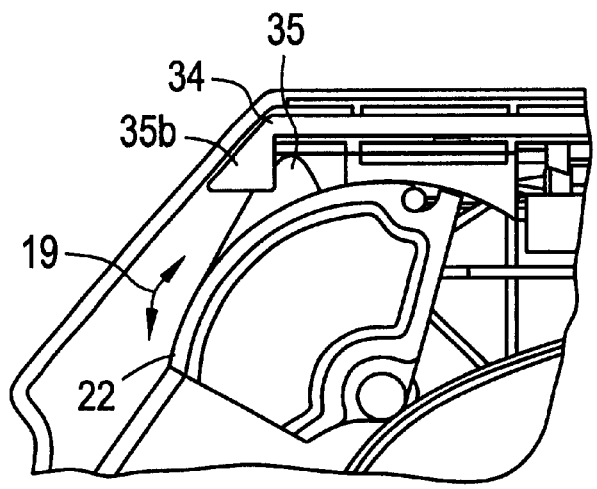
FIG. 7E is another partial cross-sectional view of the embodiment of the needle selection mechanism of FIG. 7C showing the position of the selector lever of the apparatus of FIG. 1 after the selector lever has been automatically moved responsive to forward rotation of the actuator member of the apparatus.

Another embodiment of the selection mechanism is shown in FIGS. 7C–7E in which the selection mechanism automatically positions selector lever 34 to select needle 21 as needle 20 is driven forward by actuator member 22, rather than the manual positioning of selector lever 34 described earlier. In this embodiment, the selection mechanism includes a ramp 35 coupled to actuator 22 which is sloped along surface 35a. The selection mechanism further includes a downwardly extending member 35b from selector lever 34 having a sloped surface 35c, such that when the actuator member 22 with ramp 35 rotates forward (in the direction of arrow 19a of bi-directional arrow 19), surface 35c of extending member 35b abuts and slides along surface 35a of ramp 35 to push the selector lever 34 from the left to the right (in the direction indicated by arrow 19b). FIGS. 7C–7D show the position of selector lever 34 before the selector lever is automatically moved, and FIGS. 7E–7F show the position of the selector lever 34 after the selector lever is automatically moved. The selector lever 34 need not extend through opening 12c of housing 12. In this manner, the selector lever 34 is initially positioned to the left when apparatus 10 is assembled, such that that needle 20 is pre-selected for the user to be driven, and then while the user drives the needle 20 forward, the selector lever is automatically moved to the right to select needle 21. In response, cam member 30 rotates as described earlier. When the selector lever 34 is automatically moved to its right position, the non-tissue engaging end of needle 21 will still be retained in the retainer member 28 and the non-tissue engaging end of needle 20 lies in notch 22c of the actuator member, until the actuator member fully retracts needle 20. Upon full retraction of needle 20 by actuator member 22, the needles 20 and 21 will automatically switch their positions with respect to retainer member 28 and notch 22c to enable subsequent driving of actuator 22 when needle 21 is moved forward.

Figure 7G:
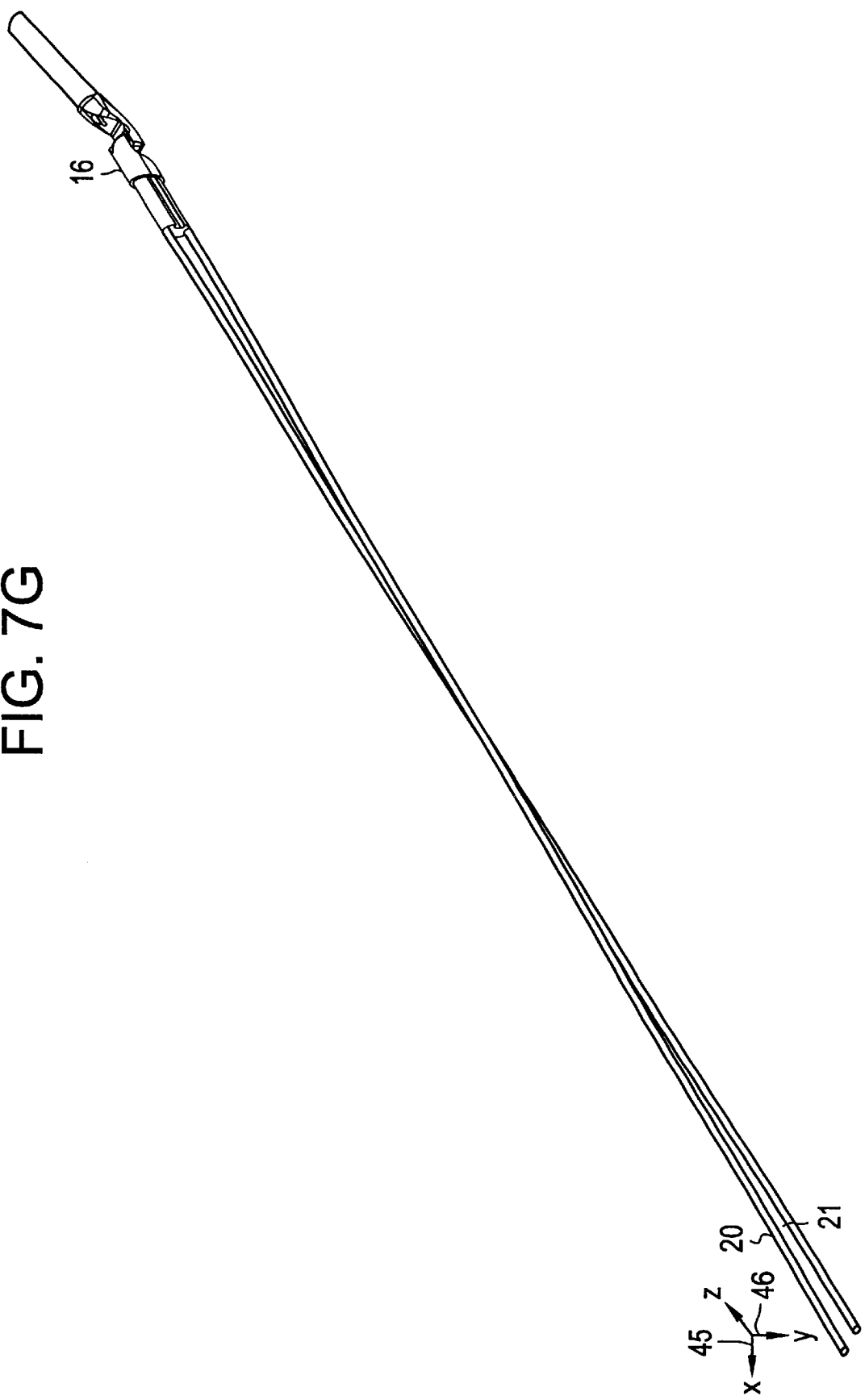
FIG. 7G is a perspective view showing the transverse of the two needles in the shaft of the apparatus of FIG. 1.

Referring to FIG. 7G, to orient the needles 20 and 21 for the tissue engagement section 16, the two needles 20 and 21 are substantially parallel in an x-z plane (parallel to the x axis 45) as they exit housing 12 into shaft 14 and then cross within the shaft to be substantially parallel in a y-z plane (parallel to the y axis 46) orthogonal to the x-z plane at the tissue engaging section 16. To maximize the separation of the needles 20 and 21, the shaft 14 is oval in cross-section having a major axis of the oval for at least a substantial portion of the shaft as it extends to shaft end 14b (FIG. 4) near the tissue engaging section 16 in the y-z plane (parallel to the y-axis 46). Near the housing 12 at shaft end 14a, the shaft 14 may be circular in cross-section (or oval in cross-section having a major axis along the plane parallel to the x-z plane), and then shaped to provide the desired oval cross-sectional shape as it extends near shaft end 14b. The shaft 14 may have an interior structure in which needles and suture tube extend in channels along the shaft from the housing to the tissue engagement section.

Referring to FIGS. 8 and 9A, the tissue engaging section 16 of the tissue suturing apparatus 10 is shown in more detail. The tissue engaging section 16 has a channel 48 for needle 20 to a first opening 50, a channel 52 for needle 21 to a second opening 54, and a channel 55 for suture tube 44 to a third opening 57. End 16a of the tissue engaging section 16 is received into shaft 14, such that edge 56 abuts the end of shaft 14. The tissue engaging section 16 has two holders or receptacles 58 and 60 which are each capable of holding a needle capturing portion 58a and 60a, respectively, received through openings 64 and 66, respectively. Needle capturing portions 58a and 60a are referred to herein as ferrules, such as described, for example, in U.S. Pat. Nos. 5,431,666 and 5,766,183, but may be any means by which a suture may be captured at the tip of a needle. The ferrules 58a and 60a each have an opening to an interior cavity shaped to enable the ferrule to frictionally engage the end of the needles 20 and 21, respectively, when received in the interior cavity. Each ferrule may be made of metal or plastic and may be oval in cross-section such that they can frictionally engage the tip of a needle. The ferrules 58a and 60a are each connected to one end of the two ends of a length of suture material or thread 62 extending through the suture tube 44 (FIG. 2). Each ferrule holder 58 and 60 has a channel 58b and 60b, respectively, through which the suture material 62 from each ferrule 58a and 60a, respectively, extends.

The tissue engaging section 16 has a first gap 68 and a second gap 70 in which the first gap 68 is along the lower side of section 16 and the second gap 70 is along the opposite upper side of section 16 and forward with respect to the first gap along the length of the section 16 in a direction distal from housing 12. The first gap 68 has two opposing surfaces 71 and 72 into which one side of a wound can be received, where opening 50 is located along surface 71 and opening 64 to ferrule holder 58 is located along surface 72 facing opening 50. Similarly, the second gap 70 has two opposing surfaces 74 and 76 into which the other side of the wound can be received, where opening 54 is located along surface 74 and the opening 66 to ferrule holder 60 is located along surface 76 and faces opening 54. Each gap 68 and 70 is shaped to have a depth to facilitate the placement of the edge of a wound therein. Surface 72, which is the distal face of the first gap 68, and surface 74, which is the proximal face of the second gap 70 both serve as stop surfaces for the tissue engaging section 16. Such stop surfaces 72, 74 assist in the placement of the tissue engaging section 16 relative to the wound as will be described further below. An opening 61 (FIG. 9B) extends through surfaces 72 and 74 of gaps 68 and 70, respectively, through which the suture material 62 from ferrule 60a passes through to opening 57 into the suture tube 44. The length of needle 21 is longer than needle 20, as shown in FIG. 9A, such that the distance from the tip of each needle to their associated ferrules 60a and 58a, respectively, are approximately equal, and thus, the amount actuator member 22 must be pivoted to drive and retract each needle is approximately equal. Ends 16a and 16b of the tissue engaging section are angled with respect to each other as shown in FIG. 9A to facilitate placement of end 16b with guide section 18 through a sheath (or cannula) and the puncture wound to maximize blood vessel engagement. The two ferrules 58a and 60a and suture material 62 may be located in apparatus 10 during manufacture. For example, the ferrules may be loaded into their associated ferrule holders, and then a wire with a hook draws the suture through opening 57 in the tissue engagement section 16 through opening 44a of the suture tube in housing 12 (FIG. 2) or tubes 43c and 43b of optional extension member 43 (FIG. 2A).

The tissue engagement section 16 may be made of metal, such as stainless steel, or other rigid biocompatible material. For example, the tissue engagement section may be made of two pieces of shaped metal having bores providing the desired openings, channels, and receptacles, joined together down the middle along section 9A—9A by welding or heat shrinking of heat shrinkable tubing connecting the two pieces. The components in the housing 12, such as the actuator member 22, selector lever 34, and needle retainer 28, may be made of molded plastic.

FIGS. 9C and 9D show the needle 20 being extended in the direction of arrow 78 into gap 68 to capture ferrule 58a upon tip 20b of the needle, and FIGS. 9E and 9F show needle 20 retracting with the captured ferrule 58a in the direction to arrow 80 into channel 48. FIGS. 10A and 10B show the needle 21 being extended in the direction of arrow 82 into gap 70 to capture ferrule 60a upon tip 21b of the needle, and FIGS. 10C and 10D show needle 21 retracting with the captured ferrule 60a in the direction to arrow 84 into channel 52. Each of the needles 20 and 21 can be manually or automatically successively selected to extend and retract the selected needle with actuator member 22 to puncture through each side of a wound, as will be described later in connection with FIGS. 17A–17H.

Figure 10E:
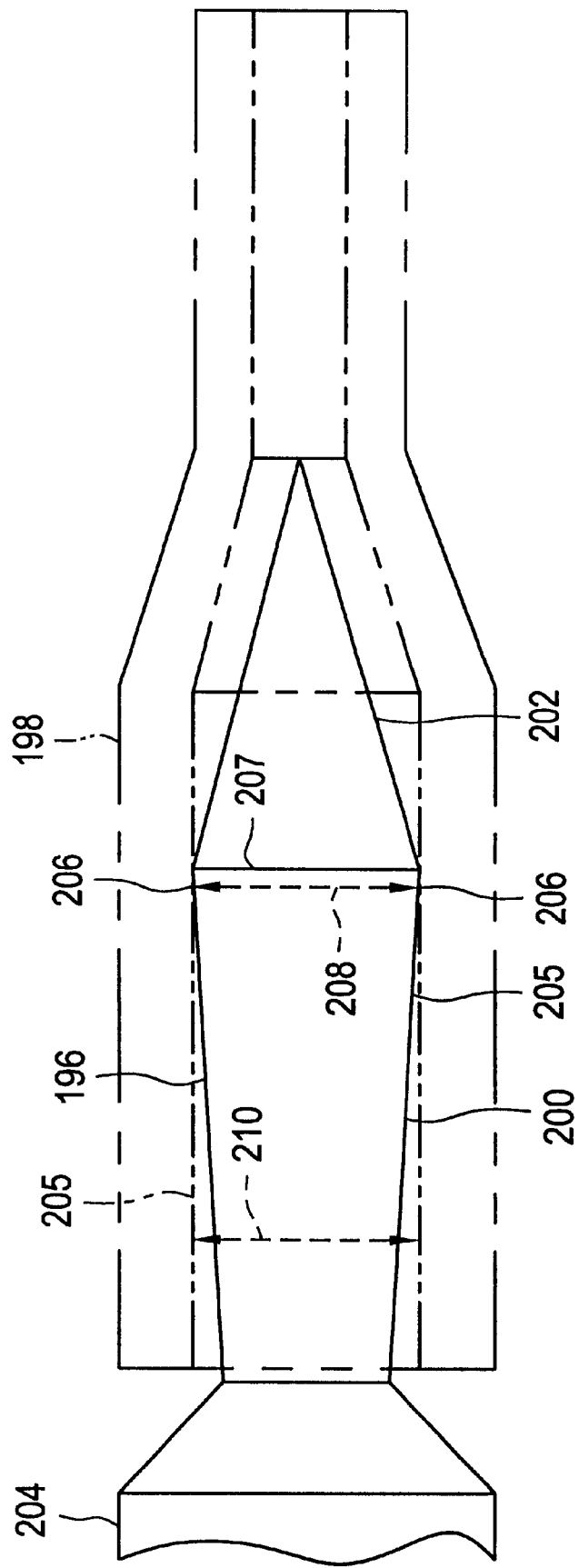
FIG. 10E is a cross-sectional view of one embodiment of the tip of each of the needles in the apparatus of FIG. 1.
Figure 11:
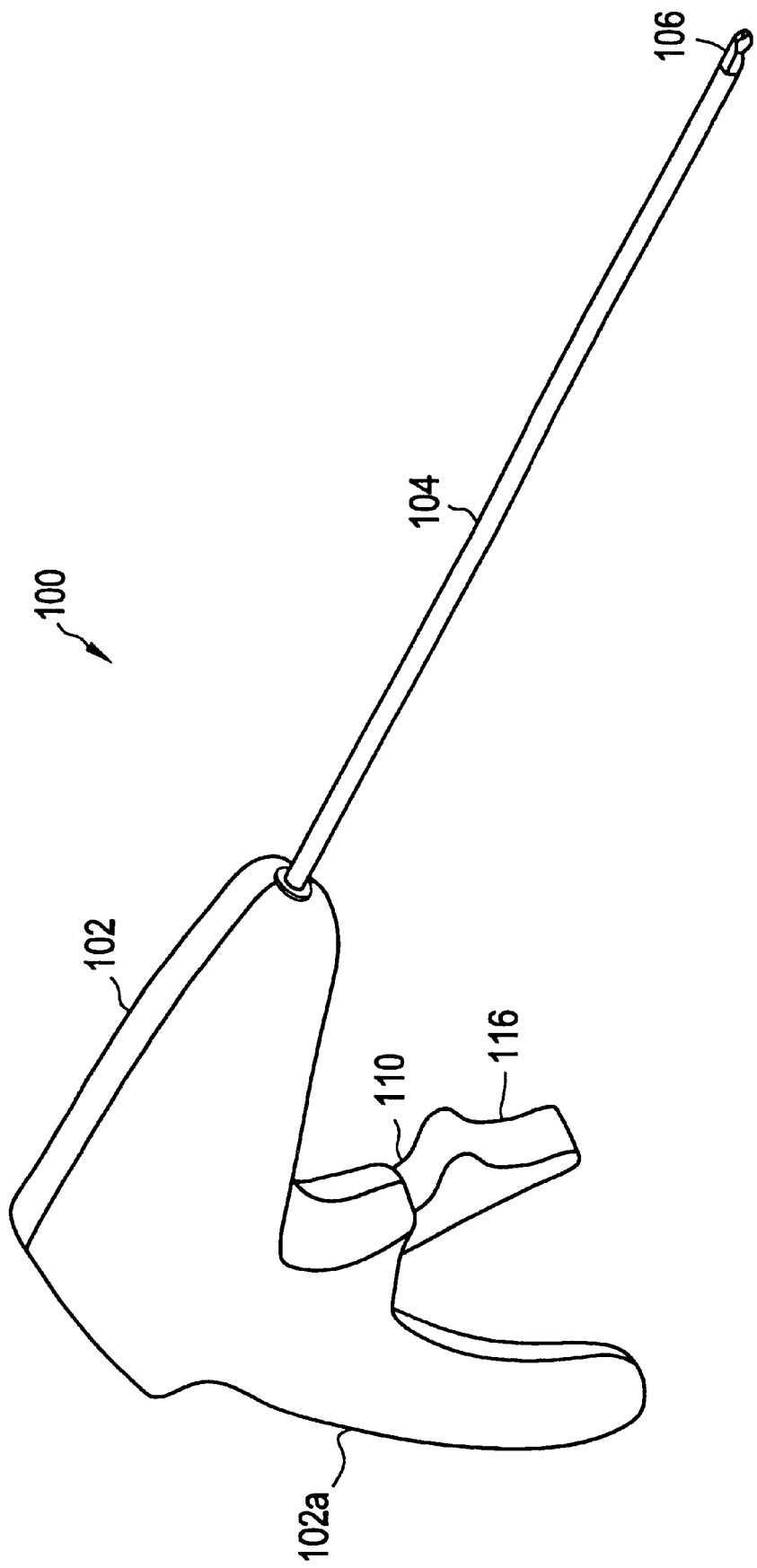
FIG. 11 is a perspective view of the suture securing apparatus in accordance with the present invention.
Figure 12:
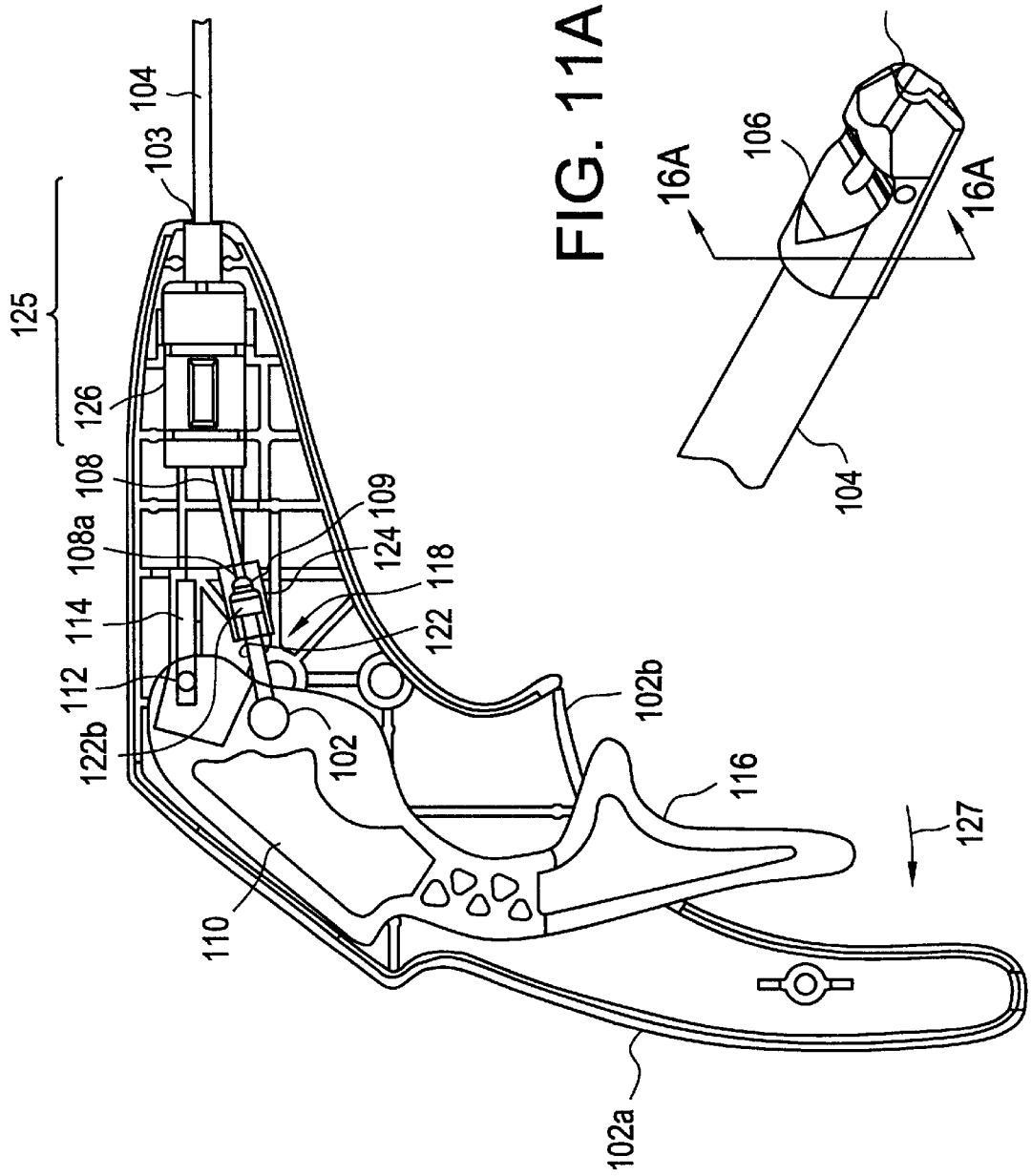
FIG. 12 is a partial side view of the suture securing apparatus of FIG. 11 in which the right cover of the housing of the apparatus is removed.
Figure 13:
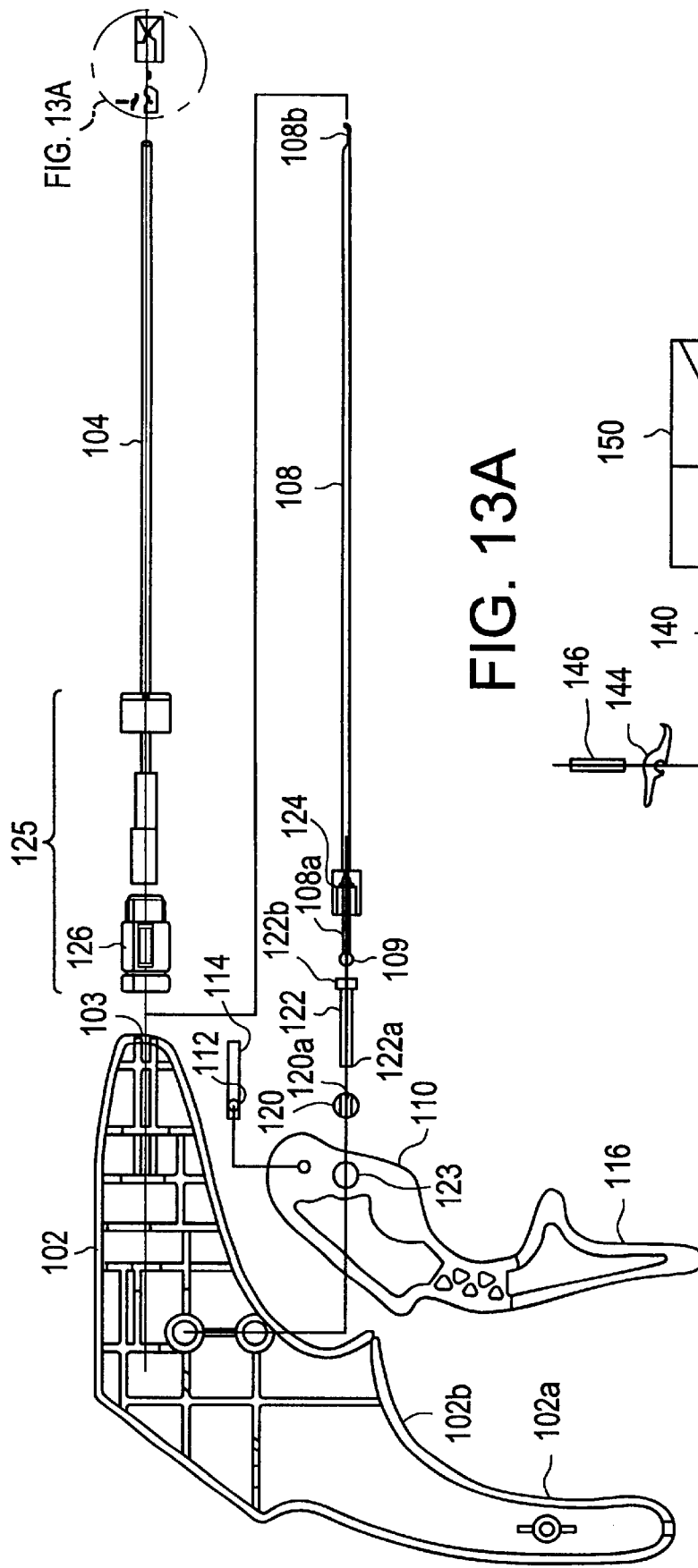
FIG. 13 is an exploded view of the suture securing apparatus of FIG. 11 in which the right cover of the housing is removed.
Figure 14:
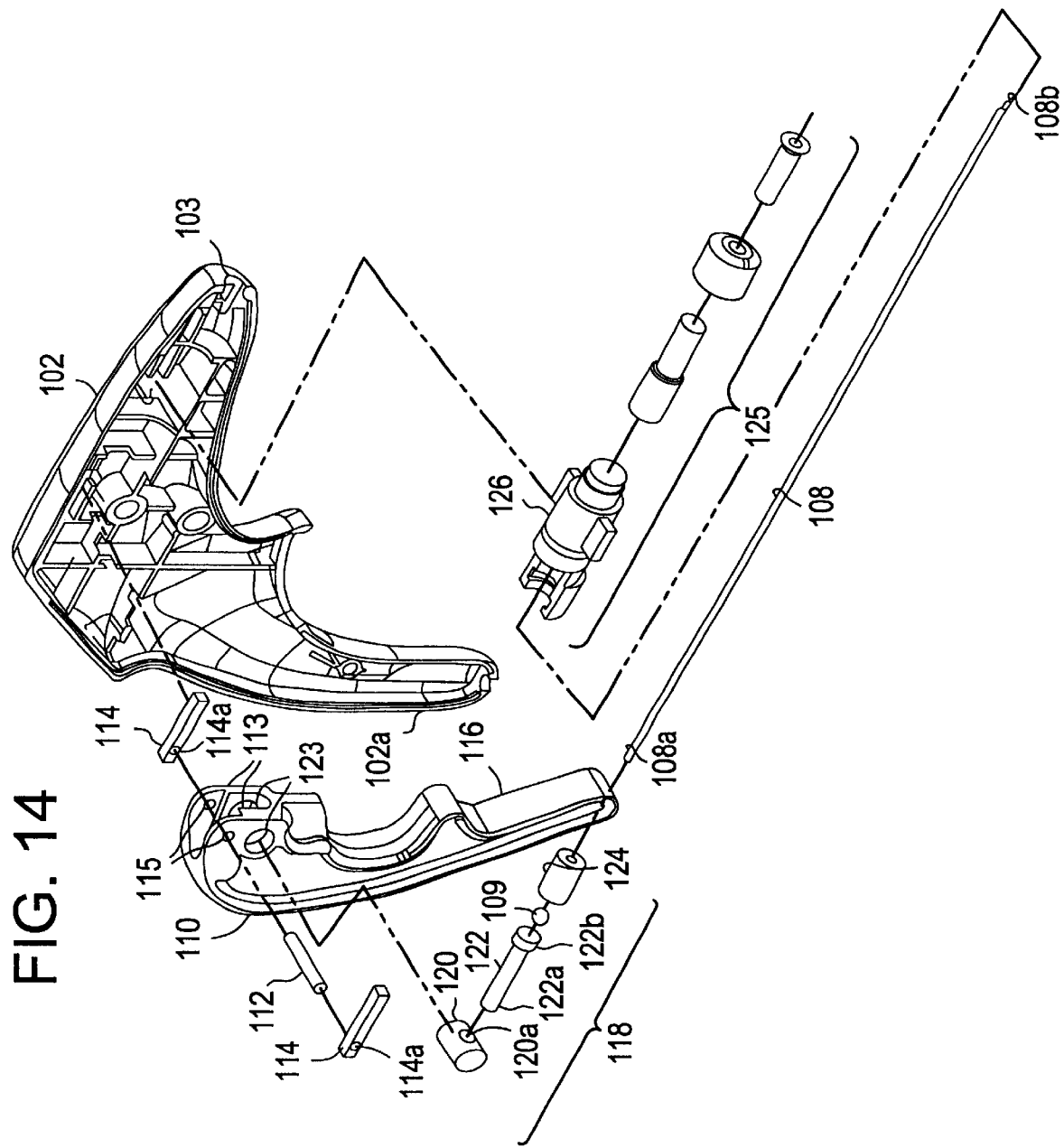
FIG. 14 is an exploded perspective view of the suture securing apparatus of FIG. 11 in which the right cover of the housing is removed.

One embodiment of the tips 20b and 21b of the needles 20 and 21, respectively, is shown in FIG. 10E. For purposes of illustration, tip 196 in the figure is exemplary of each of tips 20b and 21b of needles 20 and 21, and ferrule 198 is exemplary of ferrules 58a and 60a. Tip 196 has a region 200 before its point 202 having a surface which tapers back towards the shaft 204 of the needle, such that when the tip 196 captures a ferrule, the ferrule's interior surface 205 engages at the interface 206 of point 202 with region 200. The diameter of the tip 196 along interface 206 (indicated by arrow 208) is slightly larger than the interior width of ferrule 198 along its oval cross-section (indicated by arrow 210). For example, the ferrule's interior width may be about 0.14 to 0.18 inches and the diameter of the tip along interface 207 may be about 0.002–0.004 inches larger than the ferrule's interior width. In this manner, the ferrule may be held better onto the tip when captured by the needle. In another embodiment of tips 20b and 21b, the surface of region 200 may be parallel with the surface of shaft 204, as illustrated in needle tips 20b and 21b of FIGS. 9A, 9C–9F, and 10A–10D.

A guide section 18 is attached to end 16b (FIG. 9A) of the tissue engaging section 16. As shown best in FIG. 3, the guide section 18 has a flexible tube 18a having a conical shaped end 18b with an opening through which a guide wire may be received, and a fixed ramp member 18c located under an opening 18d in the guide section, such that a guide wire may be extended through end 18b and directed by ramp member 18c through opening 18d. The tube 18a may be made of a biocompatible plastic, like heat shrink tubing, and the ramp may be made of plastic or metal which is attached or joined within tube 18a.

Referring to FIGS. 11–14, the suture securing instrument 100 of the system is shown having a housing 102 similar to housing 12 of apparatus 10, a hollow tube 104 coupled to the housing 102 through an opening 103, and a distal end 106 coupled to tube 104. A rod 108 extends from housing 102 through tube 104 to the distal end 106. One end 108a of rod 108 is coupled to a lever 110 in housing 102. Lever 110 is pivotally mounted in housing 102 upon a pin 112 which extends through two holes 115 between upwardly extending flanges 113 of the lever. The ends of pin 112 fit into holes 114a of a pair of supporting members 114 located in the sides of housing 102. The lever 110 provides a trigger 116 extending through an opening 102b in housing 102. In the alternative, support members 114 maybe moved, such that pin 112 extends into openings within the sides of housing 102 to enable lever 110 to pivot. The lever 110 and tube 104 may be made of plastic.

The rod 108 has a spherical member or ball 109 attached at its end 108a via a hole in the ball. The ball 109 is mounted in a universal joint 118 provided by barrel-shaped member 120, adjuster shaft 122, and cover 124. Barrel-shaped member 120 extends through two holes 123 between flanges 113 of lever 110. The barrel-shaped member 120 is joined to one end 122a of an adjuster shaft 122 via a hole 120a extending through the barrel-shaped member. The other end of the adjuster shaft 122 has a socket 122b into which ball 109 is disposed. The cover 124 is a cylindrical member having an interior shaped to receive the ball 109 and socket 122b at an opening in one end, and a hole in the other end through which the rod 108 extends from ball 109.

Cover 124 holds ball 109 of rod 108 in socket 122b, but allows the ball to be movable therein.

Thus, ball 109 and socket 122b enables the rod 108 to rotate with respect to housing 102, while the barrel-shaped member 120 is rotatable in lever 110 to move the rod linearly within the slot 123a defined by flanges 113 as the housing 102 is tilted upwards or downwards. Alternatively, the lever 110 may be solid between flanges 113 and a slot provided for therein to enable the rod 108 to move linearly while barrel-shaped member 120 is rotated.

The rod 108 extends from the universal joint 118 to tube 104 through an adapter 126, which may be similar to adapter 32 of apparatus 10. Tube 104 is mounted in an assembly 125 using components similar to components 36–42 in apparatus 10. The rod 108 may be composed of a rigid wire, such as piano wire, which is sufficiently flexible to bend in adapter 126 to the universal joint 118. In the alternative, the universal joint 118 may be removed, such that ball 119 of rod 108 is captured in a socket within barrel member 120.

The distal end 106 has an interior chamber 128 into which end 108b of rod 108 is received and in linearly movable therein by a user moving trigger 116 towards handle portion 102a in the direction of arrow 127. In this manner, the end 108b of rod 108 can be retracted through the interior chamber 128 of distal end 106.

Figure 16A:
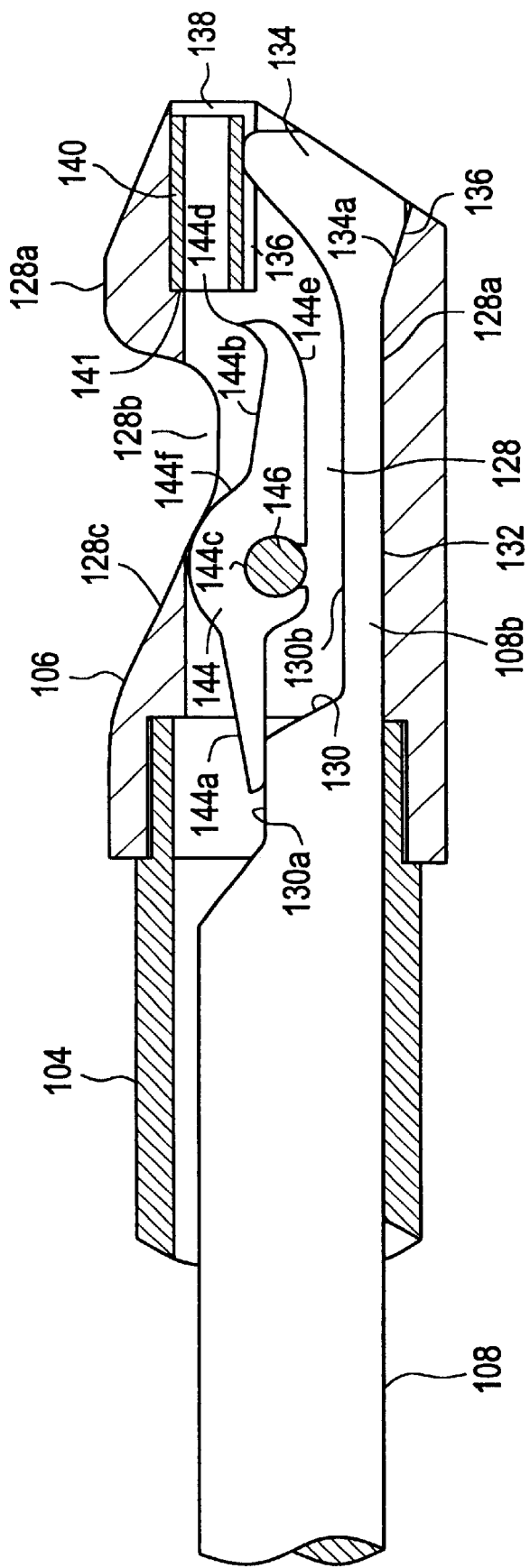
FIG. 16A is a cross-sectional view of the distal end along lines 16A—16A of FIG. 11A with a sleeve member.

Referring to FIGS. 13A, 15 and 16A, the distal end 106 and the end 108a of rod 108 are shown in more detail. End 108b of rod 108 is shaped to have a contoured upper surface 130, such as by cutting the wire by Electron Discharge Machining, or other similar wire shaping method. The upper surface 130 of end 108b, in the direction toward the tip 106a of the distal end 106, is first downwardly sloped towards tip 106a to provide a step or ledge 130a. The upper surface 130 is then further downwardly sloped after step 130a to provide a flat region 130b which is substantially parallel with the lower surface 132 of the end 108b of rod 108, and then upper surface 130 is upwardly sloped to terminate end 108b in a hammer shaped section 134. The lower surface 132 of end 108b of rod 108 is slightly downwardly sloped to form a wedge 134a along the hammer-shaped section 134. Tip 106a of distal end 106 and the lower interior surface 128d of chamber 128 is shaped to receive the hammer-shaped section 134, such as shown in FIG. 16A, in which a ramp 136 faces the wedge 134a of the hammer-shaped section 134.

Figure 16B:
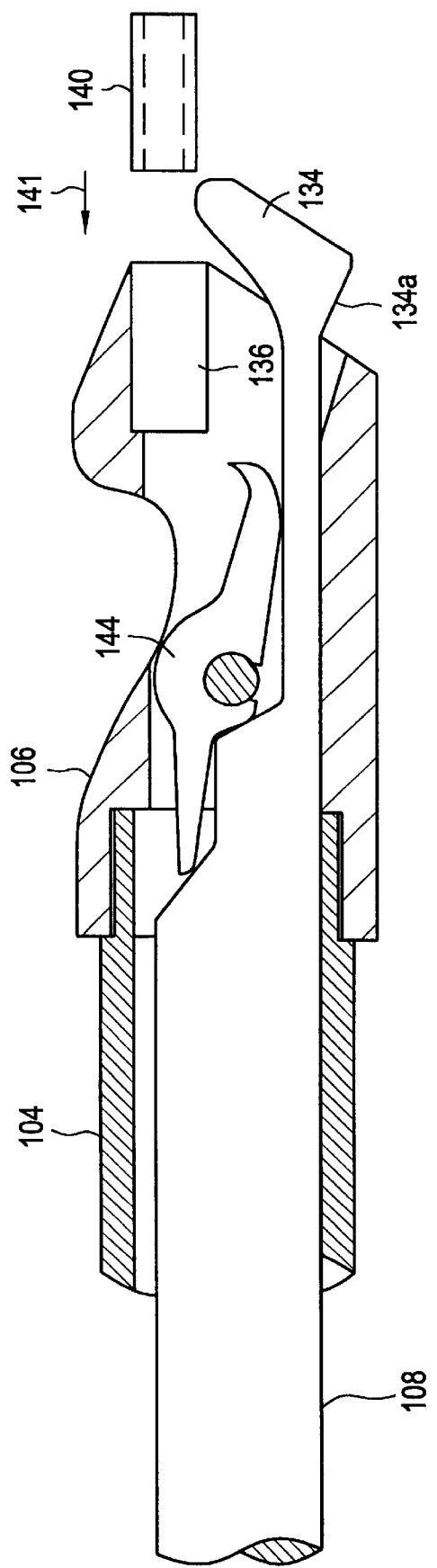
FIG. 16B is a cross-sectional view of the distal end along lines 16A—16A of FIG. 11A showing the loading of a sleeve member.

A compartment or receptacle 137 is located at tip 106a having an opening 138 through which a securing sleeve member 140 may be loaded until a stop 141 provided by a ledge in the compartment. Sleeve member 140 held in place by hammer-shaped section 134, which extends upwards through a slot 135 along the length of compartment 136. The securing sleeve member 140 may be a Ti-Knot titanium tube manufactured by LaserSurge, Inc. of Rochester, N.Y. Another slot 142 extends from the opening 138 through tip 106a to enable the hammer-shaped section 134 to pass there through when a sleeve member 140 is loaded into compartment 136, such as shown in FIG. 16B. In FIG. 16B, the sleeve member is loaded in the direction of arrow 143 by pushing forwards trigger 116 until hammer-shaped section 134 extends through slot 142. An opening 128b is provided in the top 128a of the chamber 128, such that two ends of suture material can be received through the securing sleeve member 140, when a sleeve member is loaded in compartment 136, and passed through opening 128b. The sleeve member 140 in apparatus 100 may be loaded during manufacture or by the user. The sleeve member 140 is preferably oval in cross-section as shown in FIG. 15A, such that it is pre-deformed to facilitate the crimping of the sleeve member described below. The two ends of suture material 156 are shown, for example, passing through the interior 140a of the sleeve member.

A knife 144 is pivotally mounted on a pin 146 in chamber 128. The pin 146 extends through two holes 148 on the sides of chamber 128. Knife 144 has a back portion 144a, a front portion 144b, and a U-shaped opening 144c therebetween through which pin 146 extends. Front portion 144b has an upper cutting surface 144d and a lower surface 144e. The back portion 144a of the knife may lie on step 130a to prevent the front portion 144b from rotating upwards until the cutting of suture material extending through sleeve member 140 is needed. The end 144b of the knife 144 has a ramped surface 144f to facilitate the passing of the suture material out through opening 128b. The top 128a may also have a ramped surface 128c to further facilitate the passing of the suture material out through opening 128b.

Figure 16C:
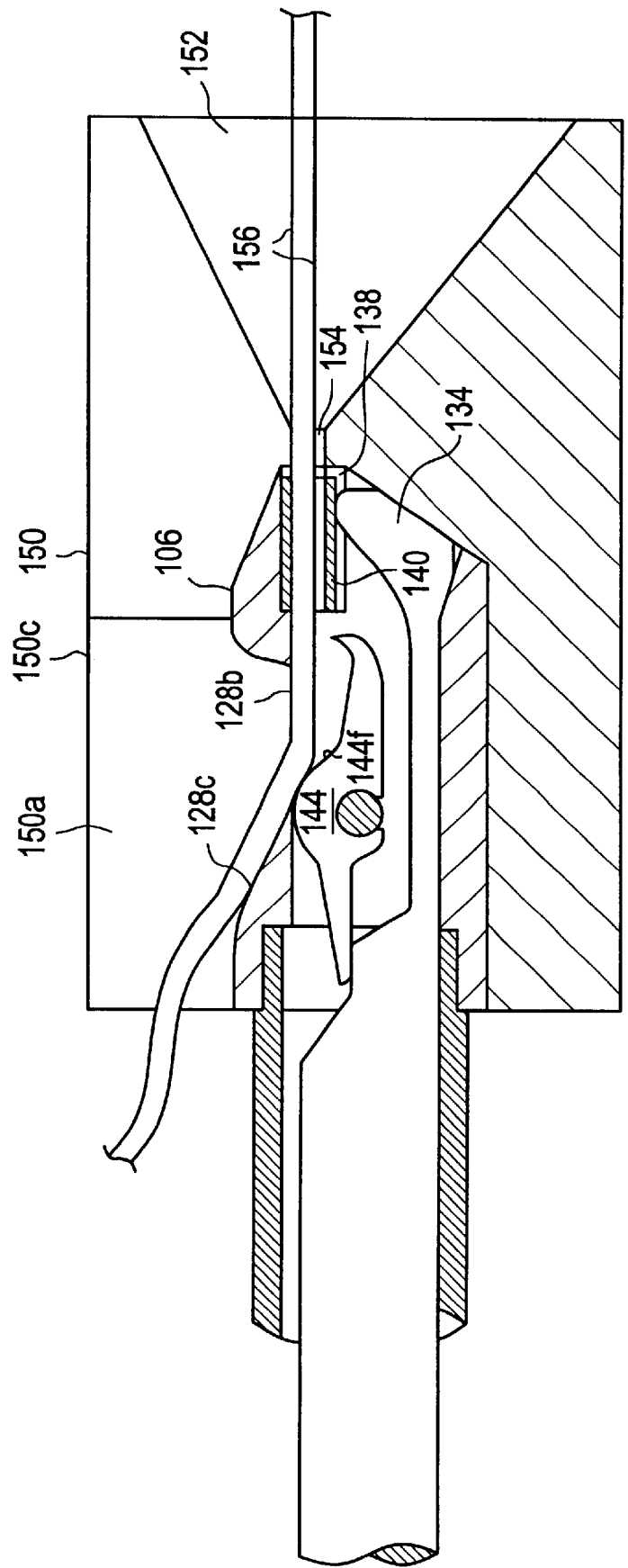
FIG. 16C is a cross-sectional view of the distal end along lines 16A—16A of FIG. 11A showing loading of the two ends of suture material with the aid of an attachment through the sleeve member of FIG. 16A.

Referring to FIGS. 16C and 16G, an optional attachment 150 may be located over distal end 106 having a funnel 152 with an aperture 154 in communication with sleeve member 140 through opening 138 to assist a user in loading the ends of the suture material 156 through the sleeve member 140 and opening 128b. The attachment 150 has an opening 150a which is shaped to receive end 106, and a slot 150b extending through the top surface 150c along the length of the attachment into which the ends of the suture material may be threaded prior to being directed through sleeve member 140. The attachment 150 is removed after the suture ends of the suture material are extended through opening 128b and grasped by the user.

Figure 16D:
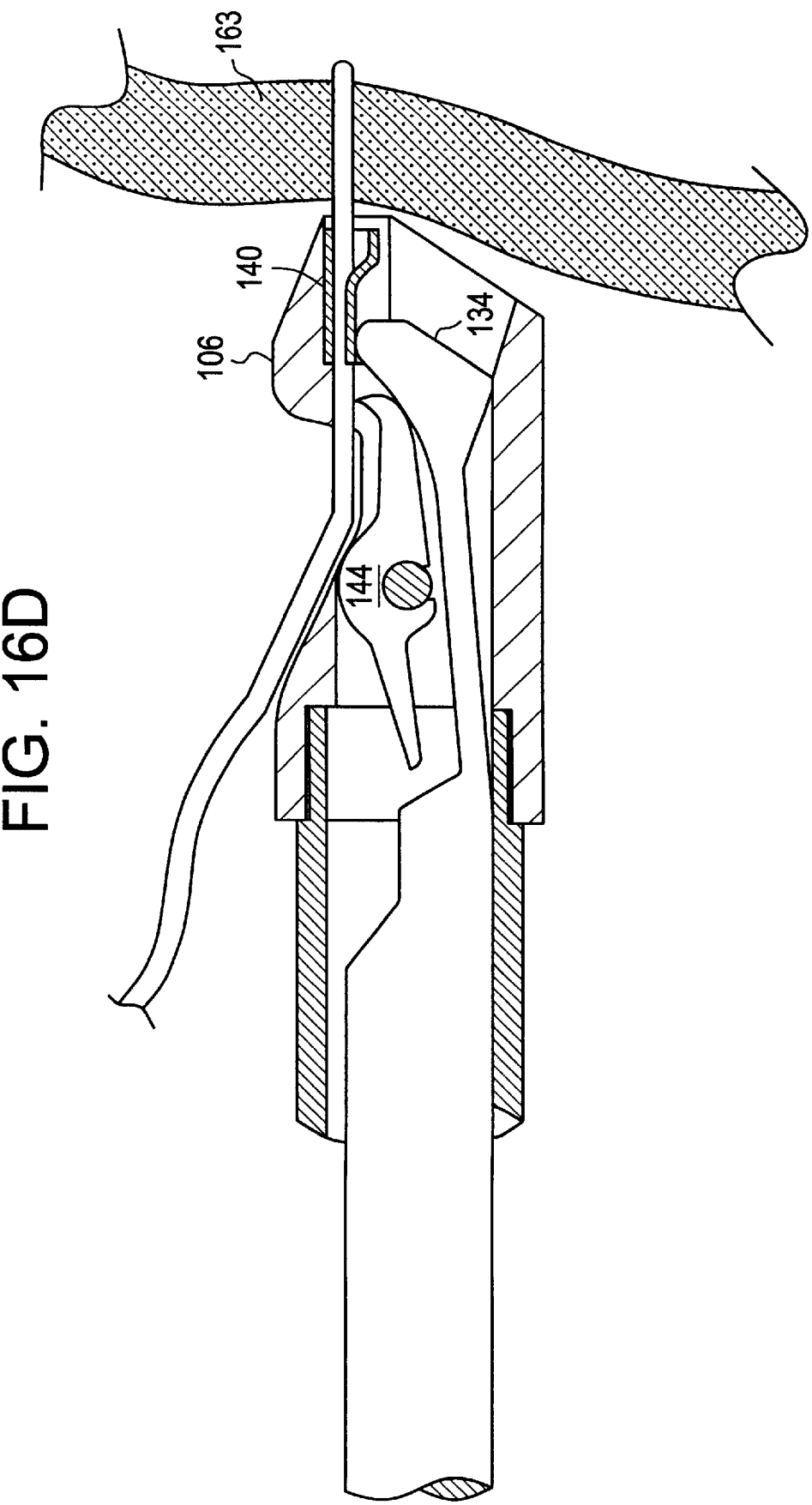
FIG. 16D is a cross-sectional view of the distal end along lines 16A—16A of FIG. 11A showing the crimping of the sleeve member of FIG. 16A.
Figure 16E:
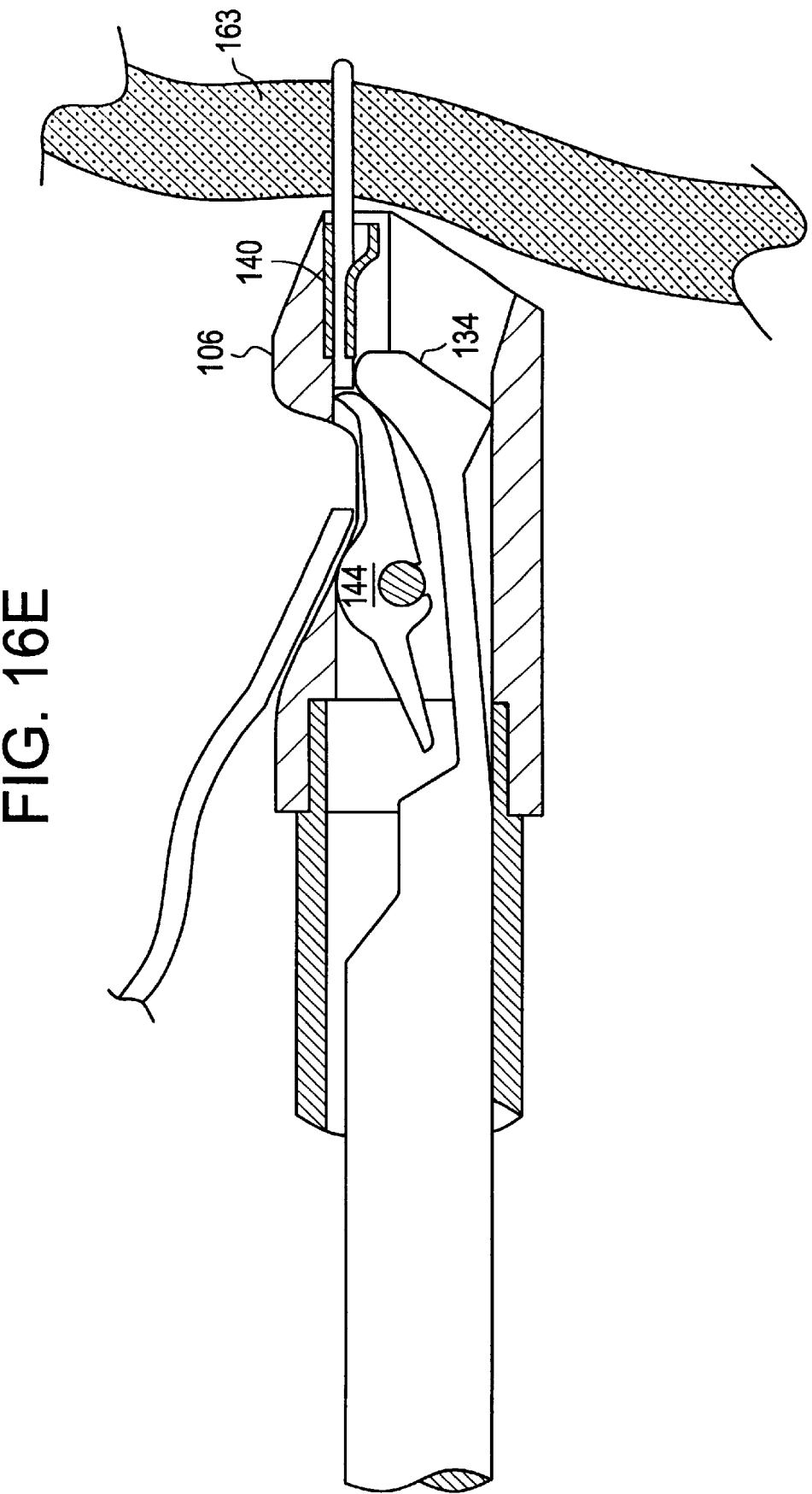
FIG. 16E is a cross-sectional view of the distal end along lines 16A—16A of FIG. 11A showing the cutting of the suture material after the sleeve member of FIG. 16A is crimped.
Figure 16F:
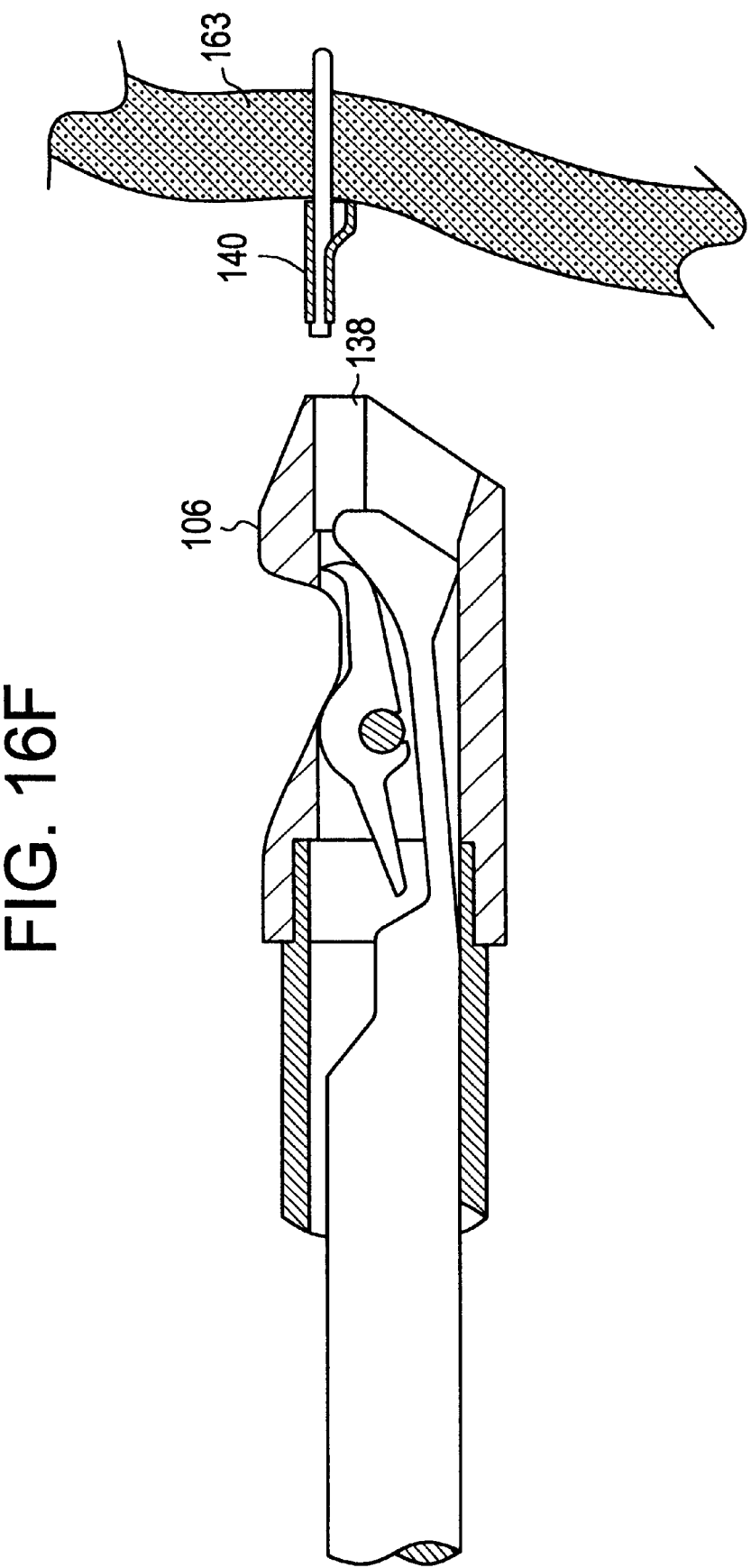
FIG. 16F is a cross-sectional view of the distal end along lines 16A—16A of FIG. 11A showing the release of crimped sleeve member of FIG. 16A from the suture securing apparatus of FIG. 11.

Once loaded with a sleeve member 140 in compartment 136 and two ends of suture material from the wound are passed through the sleeve member to exit opening 128b, a user, such as a surgeon, operates apparatus 100 by directing the apparatus through a sheath (cannula or tissue tract) through a tissue opening to the wound in tissue 163 through which the suture has been applied, such as by apparatus 10. The user applies tension to the suture material and pulls trigger 116 to retract rod 108. The retraction of rod 108 applies tension to the rod and force to raise the hammer-shaped section 134 upon ramp 136 and apply crimping pressure to substantially compress and deform at least part of the sleeve member 140, as shown in FIG. 16D. Retraction of rod 108 pulls stepped surface 130a away from the knife 144 to release it for rotation. Continued retraction of the rod 108 enables part of the upper surface 130 along hammer-shaped section 134 to abut the lower surface 144e of the knife 144, which rotates the knife upwards, such that upper cutting surface 144d of the knife cuts the suture material exiting the sleeve member 140, as shown in FIG. 16E. The crimped sleeve member 140 then is released from compartment 136 of distal end 106. Apparatus 100 may be removed from the sheath (or cannula or tissue tract). The required tension pressure on the rod applied by the user, via the lever 110, to crimp the sleeve member is substantially less than the compression force which needs to be applied by a user using the instrument described in U.S. Pat. No. 5,766,183 to crimp a sleeve member. Accordingly, apparatus 100 is easier to operate than the sleeve crimping instrument disclosed in this patent. The operation of apparatus 100 will be further described in connection with FIGS. 17K–17M.

Figure 17B:
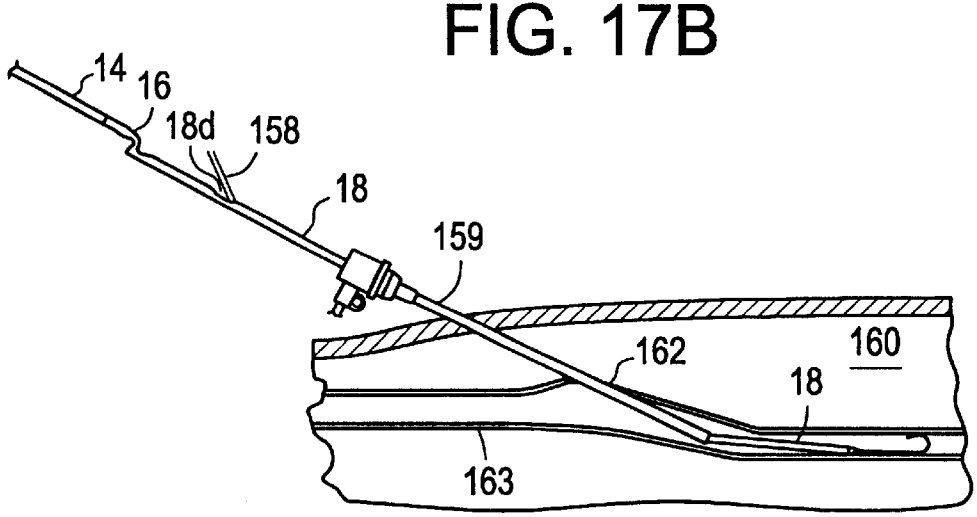
Figure 17C:
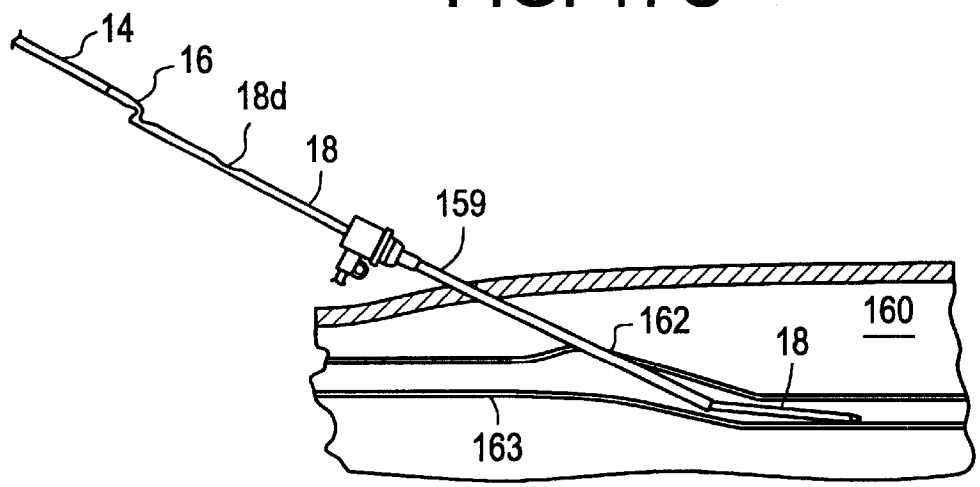
Figure 17D:
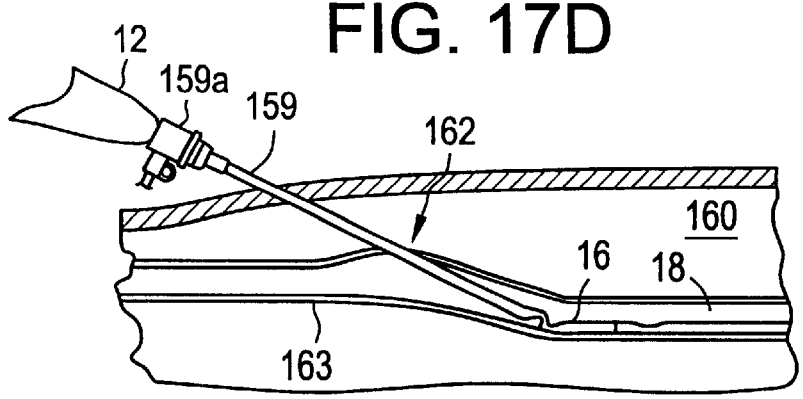
Figure 17E:
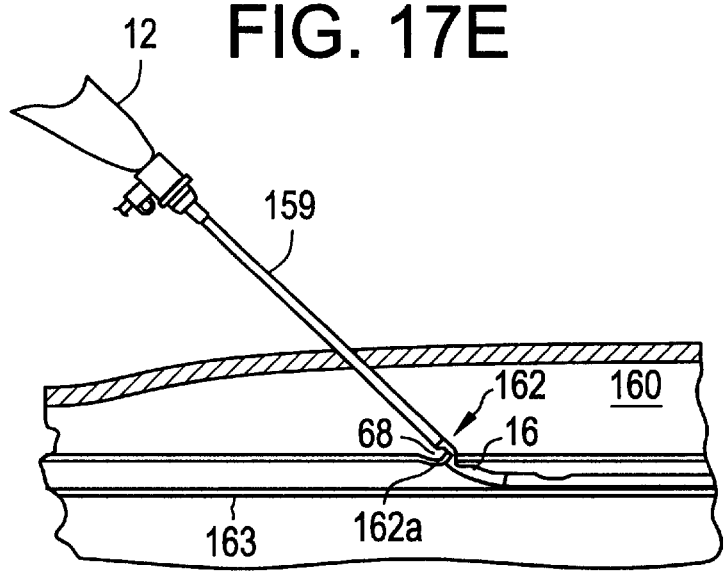
Figure 17G:
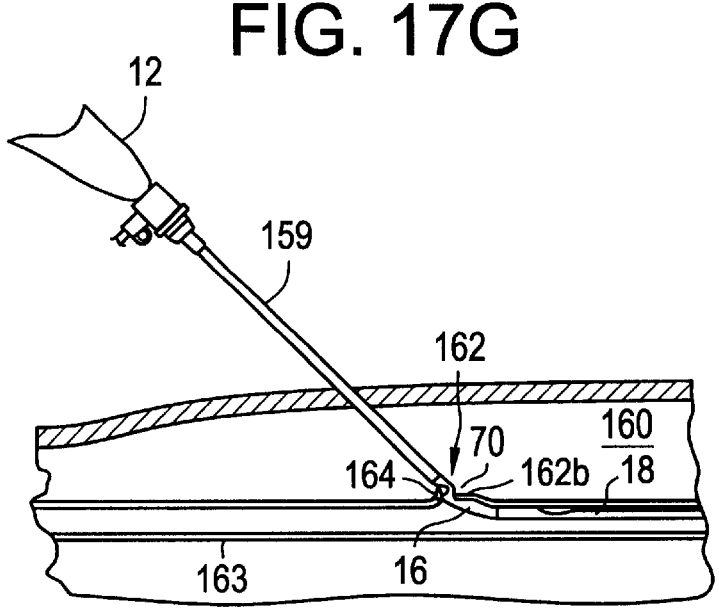
Figure 17F:
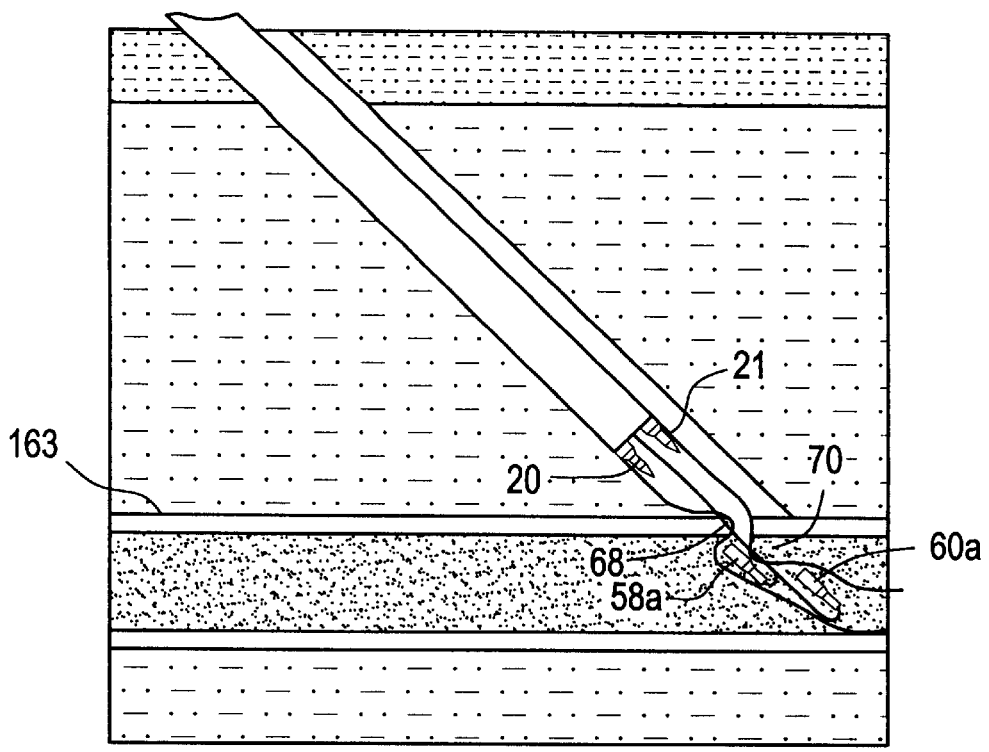
Figure 17H:
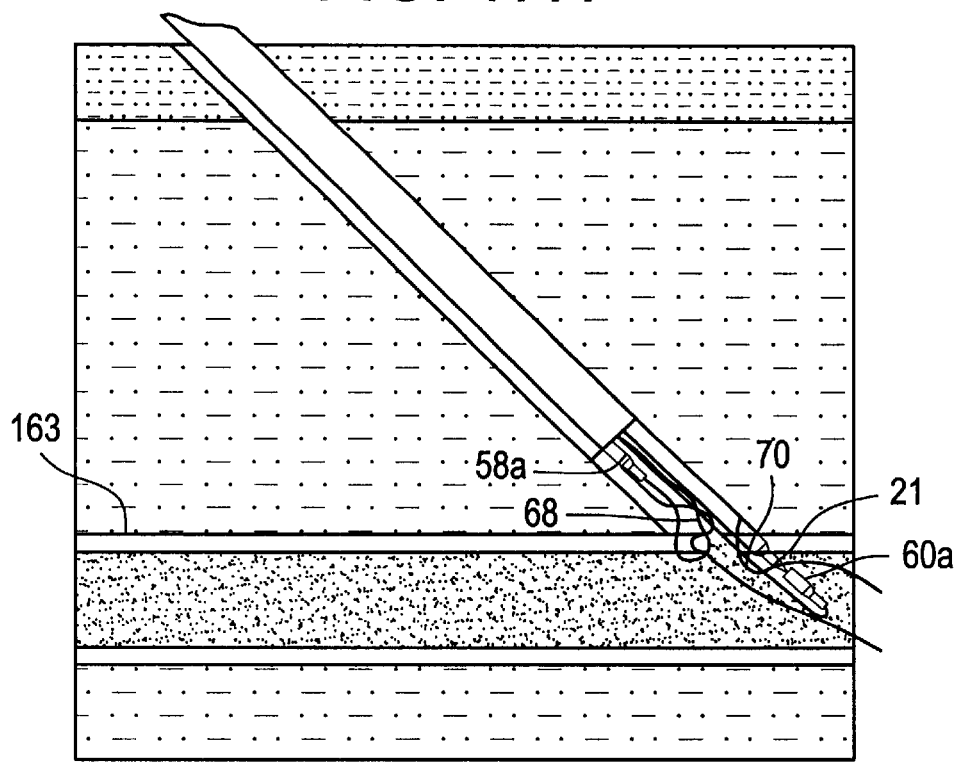
Figure 17I:
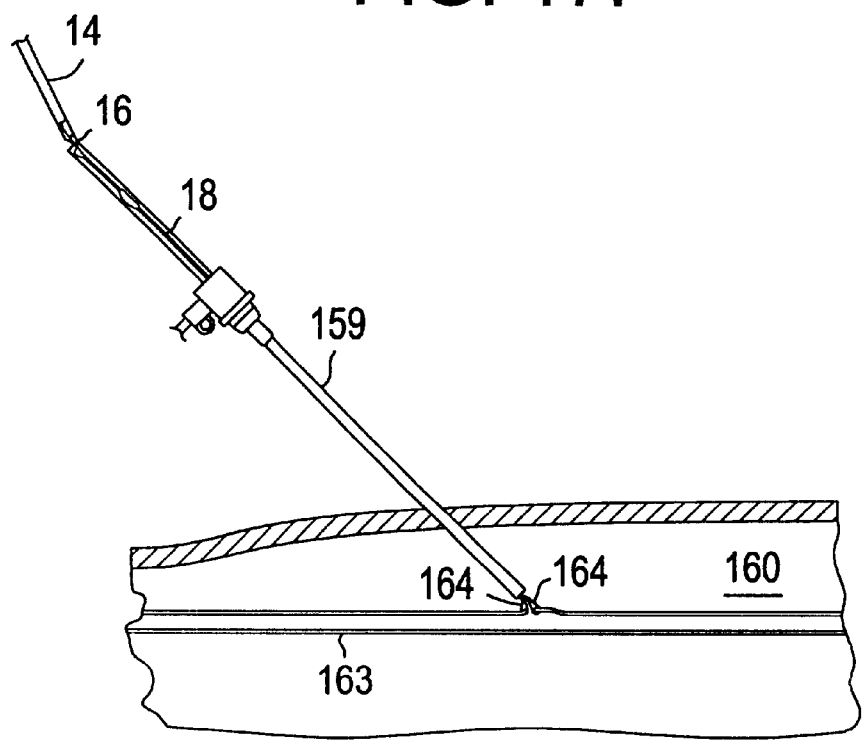

Referring to FIGS. 17A–17M, the method of closing a wound with the system of the present invention is shown. (Preferably, the apparatuses 10 and 100 are each directed through a sheath or cannula, however, they may be also be directed through a tract of tissue to a wound without a sheath or cannula.) FIG. 17A illustrates guide wire (or spring) 158 extending through a sheath 159 inserted percutaneously through skin 157 and tissue 160, and through puncture wound 162 in vessel 163. Vessel 163 may be a femoral artery, wherein puncture 162 was created to access for a catheter into the circulatory system of a patient to perform, for example, an angioplasty or angiography procedure. As shown and described herein, the distal end of guide wire 158 is directed towards the torso of the patient. Typically, a catheter (not shown) is also inserted through the sheath 159 in the wound 162. The catheter is removed prior to use of tissue suturing apparatus 10. In use, guide wire 158 is reinserted through the sheath left in the puncture wound at the end of the catherization procedure. If the selection mechanism is manual, the user verifies that needle 20 is selected, and if not, positions selector lever 34 of the selection mechanism to select needle 20. The tissue suturing apparatus 10 is threaded over the guide wire 158 by passing the guide wire 158 through opening 18d of the guide section 18 (FIG. 17B). The guide wire 159 is then removed by pulling the wire through opening 18b (FIGS. 17B and 17C). The guide section 18 of apparatus 10 reduces potential trauma to the inside of the vessel, enhance wound edge engagement and permits reinsertion of the guide wire if desired by the user. Next, the tissue engaging section 16 is passed through the sheath 159 in the wound 162 into the blood vessel 163 until the extending member 40 (FIG. 1) locks and connects apparatus 10 to the head 159a of the sheath (FIG. 17D), as described earlier. The tissue engaging section 16 is angled at its end 16b with respect to end 16a to facilitate engagement of the blood vessel wound. The user then gradually retracts apparatus 10 with its attached sheath 159 to withdraw the tissue engaging section 16 by pulling the apparatus 10 downwards and out through the wound 162 and lowers the apparatus until edge 162a of the wound is received in gap 68 (FIG. 17E). The user next pulls actuator member 22 to drive the needle 20 to puncture through the vessel in proximity of wound 162 and return with capture ferrule 58a, such that a first end of the suture material 164 is placed in the vessel tissue (FIG. 17F). If the needle section mechanism is manual, the user next selects needle 21 with selector lever 34. The user then lifts up and pushes forward apparatus 10 until edge 162b of the wound is received in gap 70 (FIG. 17G). The user then pulls actuator member 22 to drive needle 21 to puncture through the vessel 163 in proximity of wound 162 and return with capture ferrule 60a, such that a second end of the suture material 164 is placed in the vessel tissue (FIG. 17H). The wound is thus sutured from inside the blood vessel and no rotation of the apparatus 10 is needed to place the suture across the wound. If the optional extension member 43 is used, it illustrates the status of suture deployment through the tissue engagement sites on opposite sides of the wound. If this display indicates that only one suture end has been placed (i.e., only one of loop 62a or 62b (FIG. 2A) moved instead of both loops) then the apparatus 10 can be partially removed, the suture material cut and removed, the guide wire reintroduced through the guide section 18, and the closure procedure described above started again with another apparatus 10 loaded with suture material.

Figure 17J:
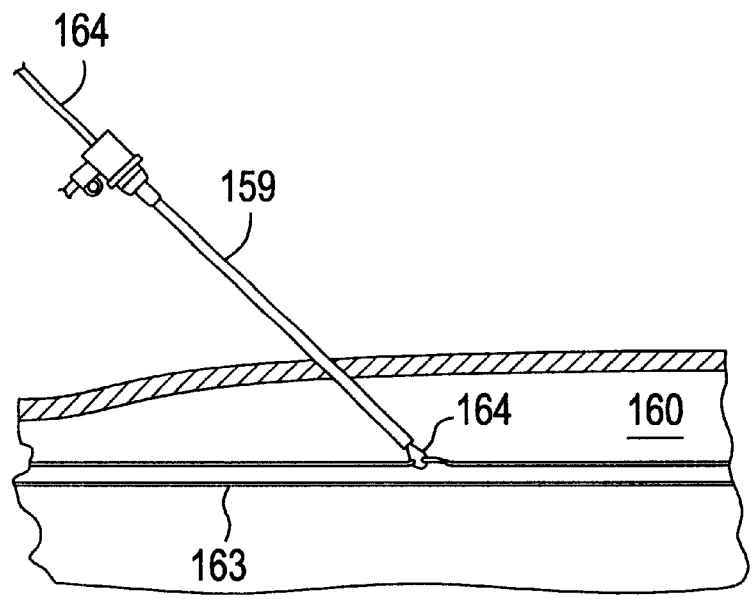
Figure 17K:
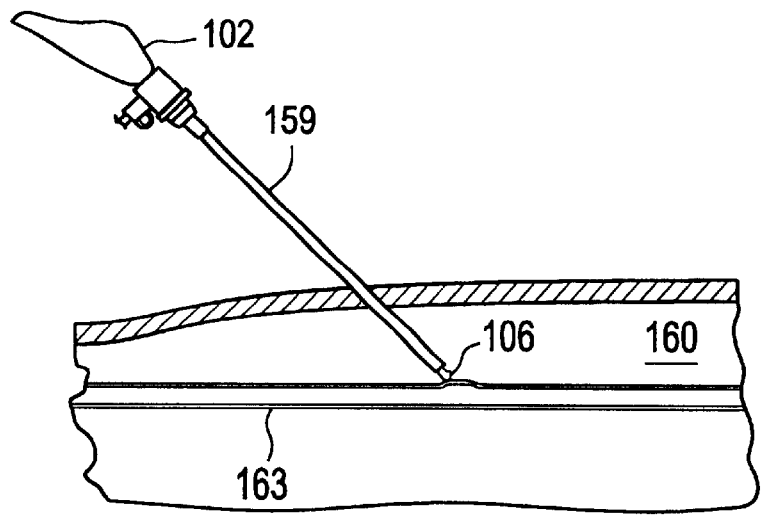
Figure 17L:
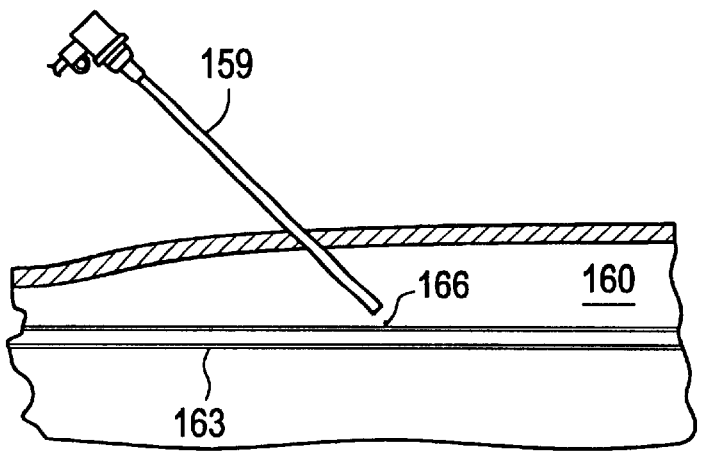
Figure 17M:
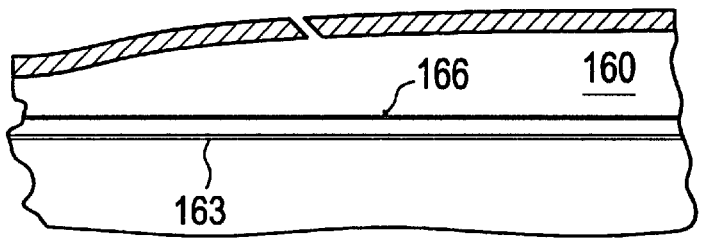

Next, the apparatus 10 is removed from the sheath 159 (FIG. 17I), and as the apparatus 10 is withdrawn, the two ends of the suture material are retained in the tissue engaging section by the ferrules captured on the needles 20 and 21, such that the suture material is drawn through the vascular tissue until a loop of suture material 164 extends across the wound 162 (FIG. 17J). The apparatus 10 may need to be rotated about 90 degrees to allow the tissue engaging section 16 to be removed from wound 162 and the blood vessel 163. The suture material 164 is then cut to release tissue engaging section 16 from the stand of suture now spanning both sides of the wound, such that the two cut ends of the suture material extend from sheath 159. The two ends of the suture material are next threaded, preferably through attachment 150, into the distal end of apparatus 100 having been loaded with a sleeve member 140, such as shown FIG. 16C. The tube 104 of apparatus 100 is then inserted into sheath 159 such that distal end 106 lies in proximity of the wound (FIG. 17K). While applying tension to the suture material 164 extending from the sheath 159, the user pulls lever 110 to crimp the sleeve member 140 and then cut the suture, as described earlier in connection with FIGS. 16D–16E. Apparatus 100 is then withdrawn from sheath 159. A small loop of suture 166 is now secured by a crimped sleeve 140a left behind to close wound 162 (FIG. 17L), as described earlier in connection with FIG. 16D. The sheath 159 is then removed from the patient (FIG. 17M), and a topical bandage may be applied.

Apparatuses 10 and 100 may be sizes to accommodate the cross-section of the sheath 159. For example, if the sheath is six French (2 mm in diameter), the size of shaft 14 and tissue engaging section 16 of apparatus 10, and the size of tube 114 and distal end 106 of apparatus 100 may be sized to accommodate this diameter. The apparatus 10 can provide, for example, bite sizes between each tissue engagement site of the suture in vascular tissue 163 and the edge of the wound of about 3 mm. Moreover, as only the needles 20 and 21 are movable in the tissue engaging section 16 of apparatus 10, apparatus 10 can be easily miniaturized to the desired application. In addition, the user can receive tactile feedback through apparatus 10 when opposing sides, representing the superior and inferior sides of the wound, are respectively received in gaps 68 and 70.

Preferably, apparatuses 10 and 100 are used in combination such as described above. However, each apparatus may also be used separately to suture a wound or seal a suture closed, respectively.

Figure 18:
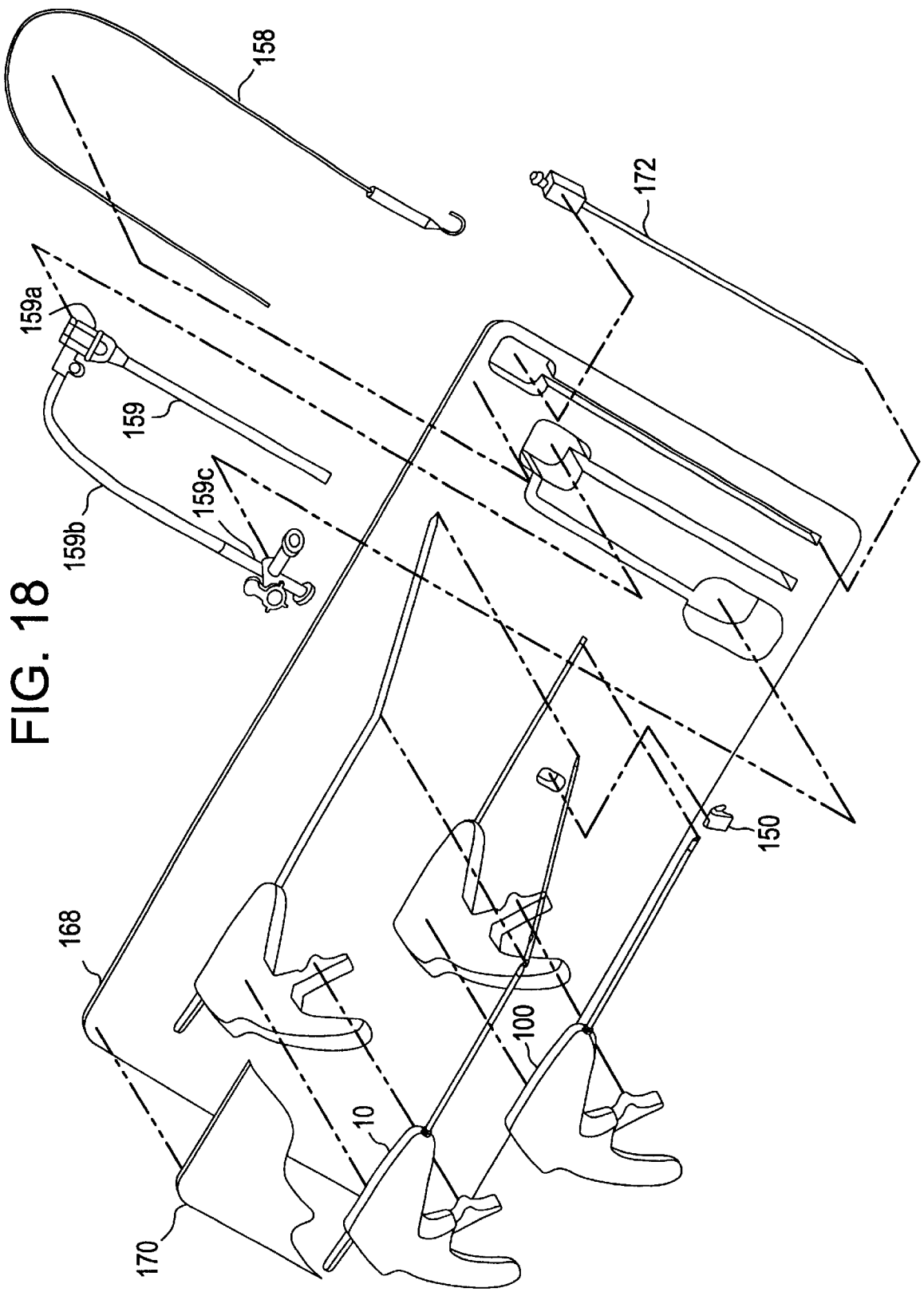
FIG. 18 shows an example of the apparatuses of FIGS. 1 and 11 included as parts of a kit.

Referring to FIG. 18, apparatus 10 and 100 may be provided as part of a surgical kit 167 useful for closing a puncture wound in a blood vessel. The kit 167 preferably includes apparatus 10, apparatus 100, sheath 159 and a dialator assembly 172. The sheath 159 has tubing 159b to valves(s) 159c through which fluid may be inserted. The kit packaging has a base 168 molded to inset the parts of the kit, and a cover 170 over the base to seal such parts therein. The base 168 can be at least partially fabricated from thermoformed plastic 602 fabricated from polyethylene fibers, such as TYVEK available from Dupont, to facilitate sterilization.

From the foregoing description, it will be apparent that there has been provided an improved system, method, and apparatuses for wound closure. Variations and modifications in the herein described system, method, and apparatuses in accordance with the invention will undoubtedly suggest themselves to those skilled in the art. For example, the use of two additional needles to needles 20 and 21 may be provided for in apparatus 10 to place an additional suture across the suture described above, such as may be desirable for closing larger diameter wounds. Such additional needles may be provided by adding two additional apertures through cam member 130 selected by selector lever 134, and two additional channels and gaps in tissue engaging section 16 substantial orthogonal to gaps 68 and 70 into which edges of the wound may be received. If needed, pledgets or bolsters may be preloaded onto such sutures to provide added tissue support. Accordingly, the foregoing description should be taken as illustrative and not in a limiting sense.

What is claimed is:

1. A tissue suturing apparatus comprising:
   a tissue engaging section having a distal end and a proximal end, a first tissue receiving gap within the tissue engaging section and a second tissue receiving gap, separate from the first tissue receiving gap, within the tissue engaging section, the first and second tissue receiving gaps facing in different directions from the tissue engaging section.

2. The tissue suturing apparatus of claim 1 wherein the first and second tissue receiving gaps are located on opposite sides of the tissue engaging section.

3. The tissue suturing apparatus of claim 2 wherein the first and second tissue receiving gaps are located on opposite perimetrical sides of the tissue engaging section.

4. The tissue suturing apparatus of claim 1 further comprising a shaft connected to a handle, the shaft attached to the proximal end of the tissue engaging section, and a guide tube attached to the distal end of the tissue engaging section.

5. The tissue suturing apparatus of claim 1 wherein the distal end of the tissue engaging section is offset angularly from the proximal end of the tissue engaging section.

6. The tissue suturing apparatus of claim 1 wherein the first and second tissue receiving gaps are displaced from each other longitudinally along the tissue engaging section.

7. The tissue suturing apparatus of claim 6 wherein the first tissue receiving gap is closer to the proximal end of the tissue engaging section than the second tissue receiving gap.

8. The tissue suturing apparatus of claim 1 wherein the first tissue receiving gap comprises a first stop surface located on a distal face of the first tissue receiving gap and the second tissue receiving gap comprises a second stop surface located on a proximal face of the second tissue receiving gap.

9. The tissue suturing apparatus of claim 8 wherein the first stop surface is angled less than 15 degrees from a perpendicular cross-section of the tissue engaging section adjacent the distal end and wherein the second stop surface is angled less than 15 degrees from a perpendicular cross-section of the tissue engaging section adjacent the proximal end.

10. The tissue suturing apparatus of claim 1 wherein a proximal face of the first tissue receiving gap and a proximal face of the second tissue receiving gap each comprise an opening leading to a channel for a needle.

11. The tissue suturing apparatus of claim 10 wherein the opening on the proximal face of the first tissue receiving gap is closer to the proximal end of the tissue engaging section than the opening on the proximal face of the second tissue receiving gap.

12. The tissue suturing apparatus of claim 1 wherein a distal face of the first tissue receiving gap and a distal face of the second tissue receiving gap each comprise an opening leading to a suture holder.

13. The tissue suturing apparatus of claim 12 wherein the suture holder is also a ferrule holder.

14. The tissue suturing apparatus of claim 13 further comprising an additional channel for holding suture material adjacent each ferrule holder.

15. The tissue suturing apparatus of claim 1 further comprising a first needle channel, a second needle channel, and a channel for suture material within the proximal end of the tissue engaging section.

16. The tissue suturing apparatus of claim 1 wherein the tissue engaging section has a substantially oval-shaped cross-section.

17. The tissue suturing apparatus of claim 1 wherein the first tissue receiving gap extends a depth greater than half a width of the tissue engaging section and wherein the second tissue receiving gap extends a depth greater than half the width of the tissue engaging section.

18. The tissue suturing apparatus of claim 1 wherein a cross section taken at the first tissue receiving gap also includes a needle channel for holding a needle adapted to pass through the second tissue receiving gap.

19. The tissue suturing apparatus of claim 1 wherein a cross section taken at the second tissue receiving gap also includes a ferrule holder for holding a ferrule adapted to be captured by a needle passing through the first tissue receiving gap.

20. A tissue suturing apparatus comprising:
a tissue engaging section having a distal end and a proximal end, a first tissue receiving gap within the tissue engaging section and a second tissue receiving gap, separate from the first tissue receiving gap, within the tissue engaging section, wherein the first and second tissue receiving gaps are displaced from each other longitudinally along the tissue engaging section.

21. The tissue suturing apparatus of claim 20 wherein the first and second tissue receiving gaps are facing in different directions from the tissue engaging section.

22. The tissue suturing apparatus of claim 20 wherein the distal end of the tissue engaging section is offset angularly from the proximal end of the tissue engaging section.

23. The tissue suturing apparatus of claim 20 wherein the first tissue receiving gap is closer to the proximal end of the tissue engaging section than the second tissue receiving gap.

24. The tissue suturing apparatus of claim 20 wherein a proximal face of the first tissue receiving gap and a proximal face of the second tissue receiving gap each comprise an opening leading to a channel for a needle.

25. The tissue suturing apparatus of claim 24 wherein the opening on the proximal face of the first tissue receiving gap is closer to the proximal end of the tissue engaging section than the opening on the proximal face of the second tissue receiving gap.

26. The tissue suturing apparatus of claim 24 wherein a distal face of the first tissue receiving gap and a distal face of the second tissue receiving gap each comprise an opening leading to a suture holder.

27. The tissue suturing apparatus of claim 26 wherein the suture holder is also a ferrule holder.

28. The tissue suturing apparatus of claim 27 further comprising an additional channel for holding suture material adjacent each ferrule holder.

29. The tissue suturing apparatus of claim 20 further comprising a first needle channel, a second needle channel, and a channel for suture material within the proximal end of the tissue engaging section.

30. The tissue suturing apparatus of claim 20 wherein the first tissue receiving gap extends a depth greater than half a width of the tissue engaging section and wherein the second tissue receiving gap extends a depth greater than half the width of the tissue engaging section.

31. The tissue suturing apparatus of claim 20 wherein a cross section taken at the first tissue receiving gap also includes a needle channel for holding a needle adapted to pass through the second tissue receiving gap.

32. The tissue suturing apparatus of claim 20 wherein a cross section taken at the second tissue receiving gap also includes a ferrule holder for holding a ferrule adapted to be captured by a needle passing through the first tissue receiving gap.

33. The tissue suturing apparatus of claim 20 wherein the first and second tissue receiving gaps are located on opposite perimetrical sides of the tissue engaging section.

34. The tissue suturing apparatus of claim 24 further comprising a needle within the channel for a needle, the needle including:
a shaft having a diameter;
a tip including a point tapering to a distal end of the needle; and,
a groove between the shaft and the tip.

35. The tissue suturing apparatus of claim 34 wherein a diameter at a proximal end of the point defines a maximum diameter of the tip, a region of the tip tapering proximally towards the shaft, wherein the region has a proximal end diameter less than the diameter of the shaft.

36. The tissue suturing apparatus of claim 35 further comprising a section between the shaft and the tip, the section tapering distally from the diameter of the shaft to the proximal end diameter of the region of the tip, the section and the region defining the groove.

37. The tissue suturing apparatus of claim 34 wherein the shaft has a substantially circular cross-section.

38. The tissue suturing apparatus of claim 34 wherein the shaft of the needle is a length adapted for receipt in the channel of the tissue suturing apparatus.

39. The tissue suturing apparatus of claim 34 wherein the shaft of the needle has a distal end adjacent the tip and a proximal end having a spherical member for receipt within a handle member of the tissue suturing apparatus.

40. The tissue suturing apparatus of claim 34 wherein the point of the needle is conically shaped.

41. A tissue suturing apparatus comprising:
 a tissue engaging section having a distal end and a proximal end, a first ferrule holder and a second ferrule holder, wherein the first ferrule holder is closer to the proximal end of the tissue engaging section than the second ferrule holder.

42. The tissue suturing apparatus of claim 41 wherein the distal end of the tissue engaging section is angularly offset from the proximal end of the tissue engaging section, and wherein the first ferrule holder and the second ferrule holder are parallel to a longitudinal axis extending through the distal end of the tissue engaging section.

43. The tissue suturing apparatus of claim 41 wherein the first ferrule holder and the second ferrule holder each include an adjacent channel for holding suture material.

44. The tissue suturing apparatus of claim 41 wherein the first ferrule holder includes a first opening for accepting a first ferrule and the second ferrule holder includes a second opening for accepting a second ferrule, wherein the first opening lies in a plane substantially perpendicular to a longitudinal axis extending through the distal end of the tissue engaging section, and wherein the second opening lies in a plane askew to the longitudinal axis extending through the distal end of the tissue engaging section.

45. A tissue suturing apparatus comprising:
 a suture tube having a single common passageway; and,
 a splitter attached to the suture tube, the splitter having a connector tube open to and sharing the common passageway, the connector tube attached to the suture tube the splitter further having a first tube and a second tube extending from the connector tube, each of the first tube and the second tube having an end open to the common passageway in the connector tube.

46. The tissue suturing apparatus of claim 45 wherein the splitter comprises a Y-shaped extension member.

47. The tissue suturing apparatus of claim 45 further comprising a loop of suture material exiting the suture tube, wherein the loop of suture material is divided into a first loop exiting the first tube and a second loop exiting the second tube, wherein movement of either side of the loop of suture material in the suture tube is detectable by viewing movement of the first loop and second loop.

48. A tissue suturing apparatus comprising:
 a suture tube;
 a splitter attached to the suture tube, the splitter having a connector tube attached to the suture tube and having a first tube and a second tube each in communication with the connector tube; and,
 a first hollow transparent member attached to the first tube and a second hollow transparent member attached to the second tube.

49. The tissue suturing apparatus of claim 48 wherein a connecting portion of the first and second hollow transparent members for connecting the first and second hollow transparent members to the first and second tubes, respectively, has a first width, and wherein the first and second hollow transparent members flare outwardly from each connecting portion to a second width greater than the first width.

50. A tissue suturing apparatus comprising:
 a suture tube; and,
 a splitter attached to the suture tube, the splitter having a connector tube attached to the suture tube and having a first tube and a second tube each in communication with the connector tube; and,
 a handle member, wherein the suture tube extends through the handle member and exits an opening in the handle member, the first and second tubes of the splitter positioned exteriorly of the handle member.

51. A kit for suturing a wound, the kit comprising:
 a tissue suturing apparatus including a first needle, a first ferrule for holding a first end of suture material, a second needle, and a second ferrule for holding a second end of suture material; and,
 a suture securing instrument including a sleeve member compartment, a rod having a hammer shaped section for crimping a sleeve member, and a knife for cutting suture material.

52. The kit of claim 51 further comprising a sheath for accepting either the tissue suturing apparatus or the suture securing instrument.

53. The kit of claim 52 further comprising a guide wire.

54. The kit of claim 51 further comprising a dilator assembly.

55. The kit of claim 51 further comprising an attachment for placement over a distal end of the suture securing instrument, the attachment having a funnel shaped opening for guiding suture material into the sleeve member compartment.

56. The kit of claim 51 wherein the tissue suturing apparatus further comprises a suture tube for holding suture material and a Y-shaped tubular extension member attached to a proximal end of the suture tube.

57. A method of approximating tissue sections, the method comprising:
 inserting a tissue suturing apparatus through the wound;
 positioning a tissue engaging section of the tissue suturing apparatus adjacent the wound;
 receiving a first edge of the wound within a first gap of the tissue engaging section;
 driving a first needle through the first gap and the first edge of the wound;
 capturing a first ferrule with the first needle, the first ferrule having an attached strand of suture material;
 drawing the first needle and captured ferrule back through the first gap and the first edge of the wound;
 receiving a second edge of the wound within a second gap, located on a longitudinally displaced portion of the tissue engaging section, of the tissue suturing apparatus;
 driving a second needle through the second gap and the second edge of the wound;
 capturing a second ferrule with the second needle, the second ferrule having an attached strand of suture material; and, drawing the second needle and captured ferrule back through the second gap and the second edge of the wound.

58. The method of claim 57 further comprising pulling an actuator member to drive the first needle and the second needle.

59. The method of claim 57 further comprising selecting the second needle with a needle selection mechanism.

60. The method of claim 57 wherein receiving a second edge of the wound within a second gap comprises lifting up the tissue suturing apparatus and pushing forward the tissue suturing apparatus.

61. The method of claim 57 wherein the suture material passes through a suture tube, the method further comprising attaching a splitter to the suture tube, the splitter having a first tube and a second tube each in communication with a connector tube, the method further comprising viewing movement of the suture material adjacent the first tube as the first ferrule is drawn through the first gap and the first edge of the wound, and viewing movement of the suture material adjacent the second tube as the second ferrule is drawn through the second gap and the second edge of the wound.

62. The method of claim 57 further comprising removing the tissue suturing apparatus from the wound.

63. The method of claim 62 further comprising angularly rotating the tissue suturing apparatus to remove the tissue engaging section, which has a distal end angled from a proximal end, from the wound.

64. The method of claim 62 further comprising cutting the suture material and freeing the tissue suturing apparatus.

65. The method of claim 64 further comprising threading the suture material into a sleeve member loaded into a suture securing instrument.

66. The method of claim 65 wherein threading the suture material into a sleeve member comprises placing an attachment over a distal end of the suture securing instrument, threading the suture material through an opening of the attachment, and removing the attachment.

67. The method of claim 65 further comprising positioning a distal end of the suture securing instrument adjacent the wound, crimping the sleeve member, and cutting the suture material.

68. The method of claim 67 wherein crimping the sleeve member comprises drawing a hammer shaped section of a rod within the suture securing instrument in a proximal direction.

69. The method of claim 68 wherein cutting the suture material comprises drawing the hammer shaped section of the rod in a proximal direction, abutting a pivotal knife with the hammer shaped section, and pivoting the knife past suture material exiting a proximal end of the sleeve member.

70. The method of claim 57 wherein inserting a tissue suturing apparatus through the wound comprises placing the apparatus at an angle approximately 30 to 45 degrees relative to the wound.

71. The method of claim 57 wherein receiving a first edge of the wound within a first gap of the tissue suturing apparatus comprises inserting the tissue engaging section within the wound, angling the tissue suturing apparatus towards the first gap, and pulling the tissue suturing apparatus in a proximal direction until a stop surface along a distal side of the first gap abuts against the first edge of the wound.

72. The method of claim 71 wherein receiving a second edge of the wound within a second gap of the tissue suturing apparatus comprises angling the tissue suturing apparatus towards the second gap and pushing the tissue suturing apparatus in a distal direction until a stop surface along a proximal side of the second gap abuts against a second edge of the wound.

73. The method of claim 57 wherein the tissue suturing apparatus includes a longitudinal axis and wherein receiving a first edge of the wound within a first gap and a second edge of the wound within a second gap includes limiting rotation of the tissue suturing apparatus about its longitudinal axis.

74. A tissue suturing apparatus comprising:
a shaft;
a first needle having a proximal end and a pointed distal end;
a second needle having a proximal end and a pointed distal end;
an actuator for driving either the first needle or the second needle through the shaft; and,
a needle selection mechanism positioned adjacent the proximal end of the first needle and the proximal end of the second needle, the needle selection mechanism arranged for selecting which needle will be driven by the actuator through the shaft.

75. The tissue suturing apparatus of claim 74 wherein the needle selection mechanism includes a movable selector lever.

76. The tissue suturing apparatus of claim 75 wherein the needle selection mechanism includes a cam member through which the first needle and the second needle extend, the cam member rotatable upon movement of the selector lever.

77. The tissue suturing apparatus of claim 76 further comprising a retainer member, wherein a proximal end of the first needle or second needle is capturable within the retainer member.

78. The tissue suturing apparatus of claim 77 wherein movement of the selector lever in one direction positions the proximal end of the first needle in the retainer member, and movement of the selector lever in an opposite direction positions the proximal end of the second needle in the retainer member.

79. The tissue suturing apparatus of claim 78 wherein the actuator includes notches for receiving whichever needle is not retained within the retainer member, the needle held within a notch of the actuator being drivable through the shaft of the tissue suturing apparatus.

80. The tissue suturing apparatus of claim 74 wherein the proximal end of the first needle includes a spherical member and the proximal end of the second needle includes a spherical member.

81. The tissue suturing apparatus of claim 74 wherein the actuator includes a pair of notches, wherein the needle selection mechanism forces one of the first needle or the second needle into one of the notches, the needle within a notch being drivable through the shaft upon movement of the actuator.

82. The tissue suturing apparatus of claim 81 wherein the spherical member abuts a proximal side of the notch for maintaining movement of the needle with the actuator.

83. A suture securing instrument comprising:
a handle member;
a hollow tube attached at its proximal end to the handle member, a distal end of the hollow tube having a tip opening allowing access to a securing sleeve member compartment and an upper wall opening allowing passage of suture material;
a knife pivotally held within the distal end of the hollow tube; and, a rod movable through the hollow tube by actuation of the handle member, the rod having a contoured distal end including a hammer shaped section;
wherein proximal movement of hammer shaped section of the rod within the hollow tube first moves the hammer shaped section past the securing sleeve member compartment and then abuts the hammer shaped section with a lower surface of the knife, pivoting an upper cutting surface of the knife towards the upper wall opening.

84. The suture securing instrument of claim 83 further comprising a securing sleeve member within the securing sleeve member compartment, wherein the securing sleeve member is crimped upon proximal movement of the hammer shaped section of the rod past the securing sleeve member compartment.

85. The suture securing instrument of claim 84 further comprising suture material threaded through the tip opening, the securing sleeve member, and out the upper wall opening, wherein the suture material is cut by the knife upon proximal movement of the hammer shaped section of the rod past the lower surface of the knife.

86. The suture securing instrument of claim 83 wherein the contoured distal end of the rod includes a step proximal to the hammer shaped section, a back portion of the knife lying upon the step to prevent the knife from pivoting towards the upper wall opening prior to proximal movement of the rod.

87. The suture securing instrument of claim 83 further comprising an attachment securable to the distal end of the hollow tube, the attachment comprising a funnel shaped opening for assisting in threading suture material into the securing sleeve member compartment.

88. The suture securing instrument of claim 83 further comprising a pin passing through opposite sides of the distal end of the hollow tube, the pin arranged for pivotally supporting the knife within the distal end of the hollow tube.

89. The suture securing instrument of claim 88 wherein the knife includes a U-shaped opening through which the pin passes.

90. A system for closure of a wound in a patient with a suture material having two ends comprising:
a first apparatus comprising a housing, a shaft having a first end and a second end in which said first end is coupled to the housing, a tissue engaging section coupled to said second end of said shaft, and a first needle and a second needle in which said first and second needles extend from the housing through the shaft into said tissue engaging section;
said tissue engaging section having a first opening and a second opening for said first and second needles, respectively, a first needle receiving portion and second needle receiving portion for said first and second needles, respectively, capable of retaining one of the ends of the suture material, and a first gap having two opposing surfaces into which one side of said wound is received in which said first opening extends through one of said opposing surfaces of said first gap and said first needle receiving portion is provided through the other of said opposing surfaces of said first gap facing said first opening, and a second gap having two opposing surfaces into which the another side of said wound is received in which said second opening extends through one of said opposing surfaces of said second gap and said second needle receiving portion is provided through the other of said opposing surfaces of said second gap facing said second opening;
means for selecting one of said first and second needles;
means in said housing for driving said selected one of said needles in which when said first needle is selected, said first needle is extendable into said first gap through said first opening to capture said first needle receiving portion and retractable into said tissue engaging section to locate a first location in said tissue through which said first end of said suture thread extends, and when said second needle is selected, said second needle is extendable into said second gap through said second opening to capture said second needle receiving portion and retractable into said tissue engaging section to locate a second location in said tissue through which said second end of said suture material extends; and
a second apparatus having means for securing a sleeve member over the two ends of the suture material to maintain said wound closed at said first and second locations in said tissue.

* * * * *